US011231378B2

(12) United States Patent
Yaroshenko et al.

(10) Patent No.: US 11,231,378 B2
(45) Date of Patent: Jan. 25, 2022

(54) X-RAY IMAGING REFERENCE SCAN

(71) Applicant: KONINKLIJKE PHILIPS N.V., Eindhoven (NL)

(72) Inventors: Andriy Yaroshenko, Garching (DE); Thomas Koehler, Norderstedt (DE); Peter Benjamin Theodor Nöel, Unterfohring (DE); Fabio De Marco, Hamburg (DE); Lukas Benedict Gromann, Freising (DE); Konstantin Willer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/650,220

(22) PCT Filed: Sep. 21, 2018

(86) PCT No.: PCT/EP2018/075643
§ 371 (c)(1),
(2) Date: Mar. 24, 2020

(87) PCT Pub. No.: WO2019/057915
PCT Pub. Date: Mar. 28, 2019

(65) Prior Publication Data
US 2020/0232937 A1 Jul. 23, 2020

(30) Foreign Application Priority Data

Sep. 25, 2017 (EP) .................................... 17192846

(51) Int. Cl.
*G01N 23/041* (2018.01)
*A61B 6/00* (2006.01)

(52) U.S. Cl.
CPC ......... *G01N 23/041* (2018.02); *A61B 6/4291* (2013.01); *A61B 6/484* (2013.01);
(Continued)

(58) Field of Classification Search
CPC .......... G01N 23/041; G01N 2223/3301; A61B 6/4291; A61B 6/484; A61B 6/488; A61B 6/582
See application file for complete search history.

(56) References Cited

U.S. PATENT DOCUMENTS

| 9,925,347 B2 | 3/2018 | Van De Molengraaf |
| 2011/0235779 A1* | 9/2011 | Ishii ....................... A61B 6/484 378/62 |

(Continued)

FOREIGN PATENT DOCUMENTS

| EP | 1731099 A1 | 12/2006 |
| JP | 201240237 A | 3/2012 |

(Continued)

OTHER PUBLICATIONS

PCT International Search Report, International application No. PCT/EP2018/075643, dated Nov. 28, 2018.

(Continued)

*Primary Examiner* — Blake C Riddick
(74) *Attorney, Agent, or Firm* — Larry Liberchuk

(57) ABSTRACT

The present invention relates to acquiring reference scan data for X-ray phase-contrast imaging and/or X-ray dark-field imaging. Therefore an X-ray detector (26) is arranged opposite an X-ray source (12) across an examination region (30) with a grating arrangement (18) arranged between the X-ray source (12) and the X-ray detector (26). During an imaging operation without an object in the examination region (30) the grating arrangement (18) is moved in a scanning motion to a number of different positions (a) relative to the X-ray detector (26) whilst the X-ray detector (26) remains stationary relative to the examination region (30) such that in the scanning motion a series of fringe patterns is detected by the X-ray detector (26). The scanning motion is repeated for a different series of fringe patterns.

(Continued)

This allows acquiring reference scan data required for calibration of an X-ray imaging device (10''') with less scanning motions.

17 Claims, 11 Drawing Sheets

(52) U.S. Cl.
CPC .............. *A61B 6/488* (2013.01); *A61B 6/582* (2013.01); *G01N 2223/3301* (2013.01)

(56) References Cited

U.S. PATENT DOCUMENTS

| | | | | |
|---|---|---|---|---|
| 2011/0243302 | A1* | 10/2011 | Murakoshi | G01N 23/041 378/62 |
| 2013/0083893 | A1* | 4/2013 | Ishii | A61B 6/4291 378/62 |
| 2014/0146945 | A1* | 5/2014 | Fredenberg | A61B 6/484 378/62 |
| 2015/0182178 | A1* | 7/2015 | Baturin | A61B 6/484 378/36 |
| 2015/0204729 | A1* | 7/2015 | Kusunose | G01B 9/02098 356/521 |
| 2016/0035450 | A1* | 2/2016 | Date | G21K 1/067 378/36 |
| 2016/0042533 | A1* | 2/2016 | Kiyohara | G06T 11/006 382/103 |
| 2016/0231258 | A1* | 8/2016 | Wen | G01N 23/041 |
| 2016/0317112 | A1 | 11/2016 | Roessl | |

FOREIGN PATENT DOCUMENTS

| | | |
|---|---|---|
| JP | 2015008884 A | 1/2015 |
| WO | WO2011070521 A1 | 6/2011 |
| WO | WO2014027333 A1 | 2/2014 |
| WO | WO2017001294 A1 | 1/2017 |
| WO | WO2017032864 A1 | 3/2017 |

OTHER PUBLICATIONS

Huang et al., "Alternative Method for Differential Phase-Contrast Imaging with Weakly Coherent Hard X-Rays", Physical Review. A 79, 013815 (2009).

Meinel et al., "Improved Diagnosis of Pulmonary Emphysema Using In Vivo Dark-Field Radiography", Investigative Radiology, vol. 49, No. 10, pp. 653-658, Oct. 2014.

* cited by examiner

X-RAY IMAGING REFERENCE SCAN

FIELD OF THE INVENTION

The present invention relates to X-ray phase-contrast imaging and dark-field imaging. In particular, it relates to an X-ray imaging device, a method for operating the X-ray imaging device, and a computer program.

BACKGROUND OF THE INVENTION

EP 1 731 099 A1 shows an interferometer for X-rays for obtaining quantitative phase-contrast images comprising an X-ray source, a diffractive element in transmission geometry, and a position-sensitive detector with spatially modulated detection sensitivity. A one- or two-dimensional phase-stepping scan can be implemented by lateral transverse movement of the diffractive element or a detector-sensitivity modulation mask with respect to the X-ray source. Furthermore, an analysis procedure can be implemented for phase-stepping scan data that comprises the steps of fitting for each element of the detector the intensity curve measured in the element to an intensity curve modeled or measured separately without the beam distortions under study, where at least one of the fit parameters is the shift of the curve along the position axis of the scan.

WO 2017/001294 A1 discloses an X-ray imaging apparatus comprising an X-ray source for emitting a beam of X-ray radiation, an X-ray detector arranged opposite said X-ray source across an examination region for accommodating an object to be imaged; and an interferometer arranged, at least partly in the beam of X-ray radiation. A footprint of said at least one grating is smaller than a footprint of a radiation sensitive area of said X-ray detector, wherein the apparatus is configured to effect, during an imaging operation, said at least one grating to move in a scanning motion relative to the X-ray detector whilst said X-ray detector remains stationary relative to the examination region.

SUMMARY OF THE INVENTION

It can be seen as an object of the present invention to provide an X-ray imaging device, a method for operating the X-ray imaging device, a computer program, and a computer-readable medium which allow deriving reference scan data for X-ray phase-contrast imaging and dark-field imaging using less scanning motions.

In a first aspect of the present invention, an X-ray imaging device is presented. The X-ray imaging device comprises an X-ray source, an X-ray detector, and a grating arrangement. The X-ray source is configured for emitting a beam of X-ray radiation. The X-ray detector is arranged opposite the X-ray source across an examination region for accommodating an object to be imaged. The grating arrangement is arranged between the X-ray source and the X-ray detector. The grating arrangement is configured to modulate onto the X-ray radiation a fringe pattern detectable by the X-ray detector. A footprint of the grating arrangement on the X-ray detector is smaller than a radiation-sensitive area of the X-ray detector. The X-ray imaging device is configured to acquire reference scan data during an imaging operation without the object in the examination region by moving the grating arrangement in a scanning motion to a number of different positions relative to the X-ray detector whilst the X-ray detector remains stationary relative to the examination region such that in the scanning motion a series of fringe patterns is detected by the X-ray detector and by moving the grating arrangement in the scanning motion to the same positions relative to the X-ray detector for a different series of fringe patterns.

As mentioned above, an X-ray detector that has a radiation-sensitive area larger than the footprint of the grating arrangement on the X-ray detector is included in the X-ray imaging device. The radiation-sensitive area of the X-ray detector is the area of the X-ray detector that is sensitive for X-ray radiation, i.e. an area occupied by pixels xy of the X-ray detector that allow detecting X-ray radiation. The footprint of the grating arrangement on the X-ray detector is the projection of the grating arrangement to the X-ray detector, i.e., the area on the X-ray detector occupied by the fringe pattern generated by the grating arrangement. Therefore, in order to provide fringe patterns to the whole radiation-sensitive area of the X-ray detector, a scanning approach is used in which the grating arrangement is moved relative to the X-ray detector. The scanning motion allows imaging an object having a size larger than the footprint of the grating arrangement, as the grating arrangement can be moved relative to the object and the X-ray detector. The scanning motion furthermore allows to overcome a lack of sufficiently large X-ray gratings for imaging large objects, such as bodies or parts of the bodies of a patient.

As mentioned above, the X-ray imaging device is configured to acquire reference scan data during an imaging operation without the object in the examination region, inter alia by moving the grating arrangement several times in the scanning motion to the same positions relative to the X-ray detector for several different series of fringe patterns. The same positions are herein to be understood to cover the exact same positions and positions with minor deviations from the exact same position, e.g. in case of a rotation of the grating arrangement around an axis extending through a focal spot of the X-ray source and relative to the stationary X-ray detector, a minor deviation of the exact same position can be in the order of milliradians or below, such as 0.075 mrad in the case that the X-ray detector has for example a pixel size of 150 μm and the distance between the X-ray source and the X-ray detector is 2 m. The minor deviations of the exact same positions may result from problems of synchronizing the scanning motion with a readout of the X-ray detector. In particular it can be in question whether a neighboring pixel is already illuminated or not. Therefore for example for reference scan data acquired with minor deviations of the same position from the exact same position, the X-ray imaging device can be configured to process the reference scan data by interpolating between neighboring positions of the exact same position in order to determine the fringe pattern at the exact same position. The X-ray imaging device can for example comprise a processing unit for processing the reference scan data.

The grating arrangement comprises one, two, three, or more gratings. Different series of fringe patterns can for example be generated by changing a relative lateral position of one or more gratings of the grating arrangement to the other gratings of the grating arrangement, by changing the position of the focal spot of the X-ray source relative to the grating arrangement and the X-ray detector, or by rotating one or more gratings of the grating arrangement relative to the X-ray detector around an axis extending through the one or more gratings and which is perpendicular to an optical axis which extends in the direction of a central beam of X-ray radiation between X-ray source and X-ray detector. Gratings of the grating arrangement can be arranged along a grating arrangement axis. The relative lateral position of a grating of the grating arrangement to other gratings of the grating arrangement can be changed by moving the grating perpendicular to the grating arrangement axis. This means that the grating can be moved horizontally or vertically in order to generate different fringe patterns if the grating arrangement axis is for example aligned with the optical axis. By changing the relative lateral position of the grating relative to the other gratings the slits of the gratings are relatively displaced perpendicular to the grating arrangement axis such that a different fringe pattern is generated.

Since the X-ray imaging device is configured to acquire reference scan data inter alia by moving the grating arrangement in the scanning motion to the same positions relative to the X-ray detector for a different series of fringe patterns, reference scan data and a corresponding full phase-stepping curve can be acquired for every pixel xy of the X-ray detector with a reduced number of different positions and reduced number of different series of fringe patterns. The acquired reference scan data can be used for calibrating the X-ray imaging device. An X-ray imaging device calibrated based on the reference scan data may add diagnostic value in particular in the area of chest imaging since the dark-field signal channel is highly sensitive to changes of the microstructure of lung tissue. For example, lung diseases like chronic obstructive pulmonary disease (COPD) and fibrosis may be accurately identified and quantified using the X-ray imaging device. Furthermore, foreign bodies on soft tissue and small fissures in bones can for example be detected by the X-ray imaging device.

The X-ray source can be any X-ray source that provides beams of X-ray radiation, such as a synchrotron or an X-ray source of sealed-tube type or rotating-anode type. A synchrotron can produce native coherent X-ray radiation. The X-ray radiation of the sealed-tube type or rotating-anode type X-ray source can be made at least partly coherent, e.g. by arranging a source grating between the X-ray source and the examination region such that the source grating generates a plurality of beams of individually coherent X-ray radiation which can be incoherent to each other. The source grating can be a grating of the grating arrangement. The emission spectrum of the X-ray source can be in the range of 25 kVp to 160 kVp, wherein kVp is peak kilovoltage, i.e. the voltage applied across the X-ray source. The emission spectrum can be a polychromatic spectrum, e.g. a polychromatic tungsten bremsstrahlung spectrum.

The gratings of the grating arrangement can have a dimension between 10 mm times 10 mm and 500 mm times 500 mm, e.g. between 426 mm times 100 mm and 426 mm times 200 mm or between 10 mm times 10 mm and 200 mm times 200 mm. Each of the gratings of the grating arrangement can have the same or a similar dimension as the other gratings or different dimensions. The footprint of the grating arrangement on the X-ray detector can have similar dimensions as the dimension of the gratings of the grating arrangement and depends on the magnification and the size of the gratings of the grating arrangement. The footprint of the grating arrangement can for example be between 10 mm times 10 mm and 500 mm times 500 mm, e.g. 426 mm times 200 mm or 426 mm times 100 mm, such that the footprint of the first grating equals the radiation-sensitive area of the X-ray detector in one dimension. Preferably, the footprint of the grating arrangement equals the entire radiation-sensitive area of the X-ray detector in a direction perpendicular to the direction of the scanning motion.

The X-ray detector can be a two-dimensional detector with pixels xy. The pixels xy can be arranged in an array. At least one pixel xy can be configured for detecting X-ray radiation. In case of no defect pixels, preferably each of the pixels xy of the X-ray detector is configured for detecting X-ray radiation. Pixel xy is the x th pixel on the x-axis and the y th pixel on the y-axis of the X-ray detector array. The X-ray detector array can be a two-dimensional array or can be made up of a number of line detector arrays arranged in parallel to each other in order to form a two-dimensional X-ray detector array. In this text parallel is to be understood as including minor deviations of a perfect parallel arrangement, for example in the order of milliradians or below, such as 0.3 mrad or 0.075 mrad, due to tolerances caused by manufacturing and installation.

During an imaging operation, the X-ray source provides X-ray radiation which propagates from the X-ray source through the grating arrangement to the X-ray detector. By passing the grating arrangement, a fringe pattern is modulated on the X-ray radiation. If the grating arrangement is moved to a different position relative to the X-ray detector, the fringe pattern detected at the X-ray detector can change. Therefore during a scanning motion instead of detecting the same fringe pattern at the X-ray detector for the different positions of the grating arrangement relative to the X-ray detector, a series of fringe patterns is detected at the X-ray detector for the different positions. The different positions can be arranged such that the entire radiation-sensitive area of the X-ray detector is provided with fringe patterns during the scanning motion along the different positions. For example if the gratings of the grating arrangement are tilted relative to the X-ray detector due to a rotating scanning motion of the grating arrangement relative to the X-ray detector and the X-ray detector is planar, the fringe pattern will hit the X-ray detector under an angle. Therefore the distances between the different pixels of the X-ray detector and the gratings of the grating arrangement are different for different pixels. Larger distances between the gratings of the grating arrangement and a pixel xy of the X-ray detector result in a larger magnification of the fringe pattern. Therefore, if the grating arrangement is moved to different positions relative to the X-ray detector, a series of fringe patterns is detected at the X-ray detector. For each one position of the different positions, only a subset of the pixels of the X-ray detector is hit by the fringe pattern of the series of fringe patterns. Thus, moving the grating arrangement to different positions relative to the X-ray detector in the scanning motion allows to receive a part of the series of fringe patterns at subsets of pixels which then allows to combine the received series of fringe patterns in order to acquire the reference scan data for all pixels of the X-ray detector.

Generating different series of fringe patterns, for example by changing the relative position of two gratings to each other or changing the position of the focal spot of the X-ray source relative to the grating arrangement and the X-ray detector, and moving the grating arrangement in the scanning motion to the same positions relative to the X-ray detector, allows to acquire a full phase-stepping curve for the pixels of the X-ray detector. The position of the focal spot of the X-ray source relative to the first grating and the X-ray detector can for example be changed by using electromagnetic or magnetic fields. Hence for acquiring the reference scan data during the imaging operation without the object in the examination region, the scanning motion is repeated, but with a different series of fringe patterns in the repetitions of the scanning motion in order to acquire further information, such as phase information at the X-ray detector. The scanning motion can for example be repeated for a number of different series of fringe patterns until reference scan data for a full phase-stepping curve is available for every pixel xy of the X-ray detector. The reference scan data as acquired can furthermore be resorted such that for every position of the grating arrangement relative to the X-ray detector, a full phase-stepping curve is available for the pixels xy of the X-ray detector. The reference scan data can for example be resorted by associating the reference scan data as acquired at a respective pixel xy for each series of fringe patterns used in the respective scanning motion to resorted data for the respective pixel xy. Hence the resorted data for pixel xy comprises a full phase-stepping curve from various positions of the grating arrangement relative to the X-ray detector and various series of fringe patterns. If, however, reference scan data is only required for a subset of pixels of the X-ray detector, the number of different positions of the grating arrangement relative to the X-ray detector in the scanning motion and/or the number of scanning motions for different series of fringe patterns can be limited to obtain reference scan data only for the subset of pixels of the X-ray detector.

The X-ray imaging device can be configured to acquire object scan data during an imaging operation with the object in the examination region by moving the grating arrangement in the scanning motion to the same positions relative to the X-ray detector used for acquiring the reference scan data for one of the series of fringe patterns.

Furthermore, the reference scan data can be used to obtain parameters that can be used in a subsequent step to fit object scan data in order to obtain an image of the object. This allows using only one of the series of fringe patterns in the scanning motion for obtaining an image of the object if the object is scanned with the same positions of the grating arrangement relative to the X-ray detector used for acquiring the reference scan data. Therefore, the number of required scans of the object can be reduced.

Preferably, only one scanning motion resulting in only one of the series of fringe patterns is used for acquiring the object scan data. Alternatively, two or more scanning motions resulting in two or more different series of fringe patterns can be used for acquiring the object scan data.

The X-ray imaging device can be configured to fit the object scan data based on parameters obtained from the reference scan data in order to obtain an image of the object. The X-ray imaging device can for example comprise a processing unit configured for fitting the object scan data based on parameters obtained from the reference scan data in order to obtain an image of the object. Alternatively or additionally an external unit, such as a personal computer, can be provided with the reference scan data and object scan data for fitting the object scan data based on parameters obtained from the reference scan data in order to obtain an image of the object.

In one embodiment, the grating arrangement comprises two gratings. The grating arrangement can also comprise three gratings or more gratings. Preferably the gratings remain in a fixed spatial relationship relative to each other during each of the scanning motions. The gratings can for example be phase gratings or absorption gratings. In one embodiment the grating arrangement comprises two absorption gratings. In another embodiment the grating arrangement comprises a phase grating and an analyzer grating, e.g., an absorption grating which enables softening the requirements on the spatial resolution of the X-ray detector for the purpose of adequately resolving a fringe pattern generated by the grating arrangement when interacting with the beam of X-ray radiation during imaging operation.

The X-ray imaging device can comprise a source grating arranged between the X-ray source and the examination region. The source grating is preferably arranged such that the source grating generates a plurality of beams of individually coherent X-ray radiation which can be incoherent to each other. The source grating can be one of the gratings of the grating arrangement. The arrangement of the source grating between the X-ray source and the examination region allows to make the X-ray radiation at least partly coherent. The X-ray imaging device preferably comprises a source grating if the X-ray source is not capable of producing native coherent X-ray radiation that is sufficiently coherent for allowing the generation of fringe patterns. The X-ray imaging device can also comprise more than one source grating and in particular an array of source gratings arranged such that at least partly coherent X-ray radiation is provided to the gratings of the grating arrangement at each of the different positions of the grating arrangement relative to the X-ray detector during the scanning motion.

The X-ray imaging device can be configured to generate different series of fringe patterns by changing a relative lateral position of the gratings of the grating arrangement to each other between subsequent scanning motions. In order to generate different series of fringe patterns for example the relative lateral position of any one or more of the gratings to the other gratings can be changed, e.g. the relative lateral position of the phase grating to the analyzer grating, the relative lateral position of the phase grating to the source grating, the relative lateral position of the source grating to the phase grating and the analyzer grating, or the relative lateral position of one of the absorption gratings to the other, et cetera can be changed. The relative lateral position of the gratings to each other can for example be changed by an actuator or the like between subsequent scanning motions. The X-ray imaging device can comprise an actuator, e.g. a piezoelectric actuator configured to move one or more of the gratings to different relative lateral positions compared to other gratings of the grating arrangement.

The X-ray imaging device can comprise a processing unit. The processing unit can be configured for processing reference scan data and object scan data by fitting a first function to the reference scan data in order to obtain the parameters and by fitting a second function to the object scan data using the parameters obtained from the reference scan data. The processing unit can alternatively be configured for processing reference scan data or object scan data.

The processing unit can be configured for fitting first function $J_{xy\alpha}(z)=I_{xy\alpha}(1+V_{xy\alpha}\cos(\phi_{xy\alpha}+2\pi z/p))$ to the reference scan data, with $J_{xy\alpha}(z)$ the reference scan data acquired at a pixel xy of the X-ray detector for position $\alpha$ of the grating arrangement relative to the X-ray detector in dependence of relative lateral position z of the gratings to each other, mean flux $I_{xy\alpha}$, fringe visibility $V_{xy\alpha}$, fringe phase $\phi_{xy\alpha}$, and grating period p.

The mean flux $I_{xy\alpha}$ is a fitting parameter corresponding to a mean intensity of the phase-stepping curve and can be defined as $$I_{xy\alpha} = \frac{1}{n}\sum_{k=1}^{n} J_{xy\alpha}(z_k)$$

with n being an integer number of different positions and $z_1, \Lambda, z_n$ being the sampled values for z, i.e. a mean intensity of the phase-stepping curve in the sense of an arithmetic mean with sum of the sampled values divided by the number of items in the sample, wherein the sampled values are reference scan data acquired at pixel xy of the X-ray detector for position $\alpha$ of the grating arrangement relative to the X-ray detector and the number of items in the sample depends on the number of different fringe patterns generated by the number of different relative lateral positions z of the gratings to each other.

The fringe visibility phase $V_{xy\alpha}$ and fringe phase $\phi_{xy\alpha}$ are further fitting parameters.

The fringe visibility $V_{xy\alpha}$ is defined as the ratio of the amplitude of $J_{xy\alpha}(z)$, and its mean, $I_{xy\alpha}$. It can be retrieved by performing a fit of measured intensities $J'_{xy\alpha}(z)$ to the model $J_{xy\alpha}(z)=I_{xy\alpha}(1+V_{xy\alpha}\cos(\phi_{xy\alpha}+2\pi z/p))$. The fringe visibility $V_{xy\alpha}$ is approximately equal to $$\frac{J'_{xy\alpha,max} - J'_{xy\alpha,min}}{J'_{xy\alpha,max} + J'_{xy\alpha,min}}$$

with $J'_{xy\alpha,max}=\max_z(J'_{xy\alpha}(z))$ the maximal and $J'_{xy\alpha,min}=\min_z(J'_{xy\alpha}(z))$ the minimal detected value of the function $J_{xy\alpha}(z)$, e.g. maximal and minimal detected intensity, at pixel xy and position $\alpha$ of the grating arrangement relative to the X-ray detector.

The fringe phase $\phi_{xy\alpha}$ is defined as the offset of the detected values of $J_{xy\alpha}(z)$ from the $\cos(2\pi z/p)$-dependence.

The grating period p is the period of the grating that is moved relatively to the other gratings in order to achieve a configuration in which the gratings have the relative lateral position z to each other, which allows to generate different series of fringe patterns during a scanning motion.

The processing unit can for example be configured to use least-squares fit or any other fitting method, e.g. weighted least-squares fit, for fitting the first function to the reference scan data. Fitting the reference scan data to the first function $J_{xy\alpha}(z)=I_{xy\alpha}(1+V_{xy\alpha}\cos(\phi_{xy\alpha}+2\pi z/p))$ allows to obtain the parameters mean flux $I_{xy\alpha}$, fringe visibility $V_{xy\alpha}$, and fringe phase $\phi_{xy\alpha}$ which can subsequently be used for fitting the object scan data. Hence, the reference scan data and the parameters obtained from the reference scan data can be used to calibrate the X-ray imaging device. The parameters can be obtained for the pixels xy of the X-ray detector, as a full phase-stepping curve for the pixels xy of the X-ray detector can be obtained from the reference scan data.

Alternatively or additionally, the processing unit can be configured for fitting second function $K_{xy\alpha}=I_{xy\alpha}T_{xy}(1+V_{xy\alpha}D_{xy}\cos(\psi_{xy}+\phi_{xy\alpha}+2\pi z_0/p))$ to the object scan data, with $K_{xy\alpha}$ being the object scan data acquired at the pixel xy of the X-ray detector, for the position $\alpha$ of the grating arrangement relative to the X-ray detector, for relative lateral position $z_0$ of the gratings to each other, image of object transmission $T_{xy}$, dark-field $D_{xy}$, and differential phase $\psi_{xy}$. The processing unit can for example be configured to use least-squares fit or any other fitting method, e.g. weighted least-squares fit, for fitting the second function to the object scan data. Furthermore, the parameters obtained by fitting the reference scan data using the first function can be used. Fitting the second function $K_{xy\alpha}=I_{xy\alpha}T_{xy}(1+V_{xy\alpha}D_{xy}\cos(\psi_{xy}+\phi_{xy\alpha}+2\pi z_0/p))$ to the object scan data allows to obtain the images of object transmission $T_{xy}$, dark-field $D_{xy}$, and differential phase $\psi_{xy}$.

The object transmission $T_{xy}$ is defined as a factor by which an X-ray detector signal at pixel xy is attenuated upon arranging the object in the examination region, while parameters z and $\alpha$ are kept constant: A mean X-ray detector signal is reduced from a given value $J_{xy\alpha}$ to $J_{xy\alpha}\cdot T_{xy}$, with $0<T_{xy}<1$. $T_{xy}$ is therefore a measure for the degree of attenuation of X-ray radiation by the object arranged in the examination region.

Dark-field $D_{xy}$ is defined as a factor of reduction of visibility $V_{xy\alpha}$ upon arranging the object in the examination region. Performing an imaging operation with the object in the examination region decreases all measured visibilities $V_{xy\alpha}$ to $D_{xy}\cdot V_{xy\alpha}$, with $0<D_{xy}<1$. The reduction of visibility is due to small-angle scatter of X-rays in the object, as well as beam-hardening effects.

The differential phase $\psi_{xy}$ is defined as a change in lateral shift of the function $J_{xy\alpha}(z)$ upon arranging the object in the examination region. Performing an imaging operation with the object in the examination region changes the lateral shift of (co-)sinusoidal oscillation from $\phi_{xy\alpha}$ to $\phi_{xy\alpha}+\psi_{xy}$, with $-\pi<\psi_{xy}<\pi$. The lateral shift is caused by refraction of X-ray radiation within the object.

Hence, the images of object transmission $T_{xy}$, dark-field $D_{xy}$, and differential phase $\psi_{xy}$ can be obtained in the imaging operation with the object in the examination region with only one scanning motion along the same positions of the grating arrangement relative to the X-ray detector that were used for acquiring the reference scan data as only one relative lateral position $z_0$ of the gratings to each other has to be used.

The X-ray imaging device can comprise a scan arm, such as a rotatable scan arm or a moveable scan arm. The scan arm can be configured for moving the grating arrangement in the scanning motion to a number of different positions relative to the X-ray detector whilst the X-ray detector remains stationary relative to the examination region such that in the scanning motion a series of fringe patterns is detected by the X-ray detector. The scan arm can furthermore be configured for moving the grating arrangement in the scanning motion to the same positions relative to the X-ray detector for a different series of fringe patterns. Therefore, reference scan data can be acquired by performing several swings of the rotatable scan arm using different relative lateral positions of the gratings to each other, wherein only the position of one of the gratings is changed.

The rotatable scan arm can alternatively or additionally be configured for rotating, during an imaging operation, the X-ray source in a scanning motion relative to the X-ray detector around an axis extending through the X-ray source whilst the X-ray detector remains stationary relative to the examination region. The X-ray source can alternatively be stationary relative to the examination region and/or the X-ray detector. In case that the X-ray source is not rotated together with the grating arrangement the emission spectrum and intensity of the X-ray source that create the fringe pattern can change during the scanning motion over the radiation-sensitive area of the X-ray detector as the X-ray source does typically not provide spherically symmetric X-ray radiation.

The X-ray imaging device can be configured to acquire reference scan data during an imaging operation without the object in the examination region by moving the grating arrangement in the scanning motion to at least four, for example 4 to 50 or 4 to 100, different positions relative to the X-ray detector whilst the X-ray detector remains stationary relative to the examination region such that in the scanning motion a series of fringe patterns is detected by the X-ray detector and by moving the grating arrangement in the scanning motion to the same positions relative to the X-ray detector for at least three, for example 3 to 12, 3 to 30, or 3 to 50, different series of fringe patterns. A lower number of scanning motions with different series of fringe patterns reduces both acquisition time and image quality. The number of scanning motions with different series of fringe patterns can be chosen such that the tradeoff between acquisition time and image quality for the respective application is optimized. A lower number of different positions of the grating arrangement relative to the X-ray detector in the scanning motion reduce image quality, image coverage, problems with mechanical accuracy, dose of X-ray radiation provided to the imaged object, and acquisition time. The number of different positions of the grating arrangement relative to the X-ray detector in the scanning motion can be chosen such that a tradeoff between image quality, image coverage, problems with mechanical accuracy, dose of X-ray radiation provided to the imaged object, and acquisition time is optimized. In order to cover a certain field of view, e.g., the entire radiation-sensitive area of the X-ray detector, the number of different positions of the grating arrangement relative to the X-ray detector in the scanning motion has to be equal or larger than the field of view divided by the footprint of the grating arrangement on the X-ray detector, such that during an imaging operation the field of view, e.g. the entire radiation-sensitive area, is provided with fringe patterns. Preferably the X-ray imaging device is configured to move the grating arrangement in the scanning motion to a number of different positions relative to the X-ray detector such that a certain field of view, e.g. the entire radiation-sensitive area of the X-ray detector, is covered between 3 to 10 times.

The grating arrangement is arranged at least partly in the beam of X-ray radiation during the imaging operation. The X-ray imaging device can be used for performing X-ray phase-contrast imaging and/or dark-field imaging.

In one embodiment the grating arrangement comprises a phase grating and an absorption grating. The distance between the gratings can be tuned to fit the requirements of Talbot distance such that the grating arrangement forms a Talbot-Lau type interferometer. The requirements of Talbot distance are for example disclosed in EP 1 731 099 A1, in particular in paragraphs [0053] to [0058]. The Talbot-Lau type interferometer can comprise a source grating, a phase grating and an absorption grating. The absorption grating can function as an analyzer grating.

Alternatively the grating arrangement can also comprise two absorption gratings and the gratings can be arranged such that the X-ray imaging device allows performing X-ray phase-contrast imaging and/or dark-field imaging. The gratings can for example be arranged in one of the grating arrangements disclosed in Huang et al. "Alternative method for differential phase-contrast imaging with weakly coherent hard x rays", Phys. Rev. A 79, 013815 (2009), in particular in section II.B and II.C. These grating arrangements comprise two absorption gratings. In one embodiment of the X-ray imaging device periods $p_1$ and $p_2$ of the two absorption gratings of the grating arrangement are adjusted such that $$\frac{p_1}{p_2} = \frac{L}{L+D},$$

with distance L between the X-ray source and the first absorption grating and distance D between the first absorption grating and the second absorption grating. In another embodiment of the X-ray imaging device that comprises a source grating and two absorption gratings, the periods $p_1$ and $p_2$ of the two absorption gratings of the grating arrangement are adjusted such that $$\frac{p_1}{p_2} = \frac{L_s}{L_s + D}$$

and a period $p_0$ of the source grating of the grating arrangement is adjusted such that $$p_0 = m\frac{L_s}{D}p_2,$$

with distance $L_S$ between the source grating and the first absorption grating, distance D between the first absorption grating and the second absorption grating, and positive integer m. The X-ray imaging device comprising two absorption gratings allows to obtain phase-contrast images with less strict distance requirements for the gratings than an X-ray imaging device with a Talbot-Lau interferometer.

Alternatively the X-ray imaging device can also comprise any other grating arrangement that allows performing X-ray phase-contrast imaging and/or dark-field imaging.

The different positions of the scanning motion can be arranged on a circular path, straight path, a curved path, an arcuate path, a polygonal path, or any other path. The different positions can be arranged such that an essentially horizontal or vertical scanning motion can be performed. In this text, horizontal means a direction perpendicular to gravity. Likewise, in this text, vertical means a direction parallel to gravity. An object, such as a patient can be imaged in a standing position or a lying position, i.e., the object in standing position can be imaged using a horizontal or vertical scanning motion along any one of the paths the different positions are arranged along and the object in a lying position can be imaged using a horizontal or vertical scanning motion along any one of the paths the different positions are arranged along.

The X-ray imaging device can for example be used in a clinical environment, such as a hospital, for medical imaging. In particular medical imaging, such as mammography and chest imaging can be performed using the X-ray imaging device. The X-ray imaging device can also be used in an industrial environment. In particular in non-destructive testing and security scanning, such as scanning of luggage, containers, and the like.

In a further aspect of the present invention, a method for operating the X-ray imaging device according to claim 1 or any embodiment of the X-ray imaging device is presented. The method comprises the steps:

moving the grating arrangement in a scanning motion to a number of different positions relative to the X-ray detector, while keeping the X-ray detector stationary relative to the examination region, such that in the scanning motion a series of fringe patterns is detected by the X-ray detector, and moving the grating arrangement in the scanning motion to the same positions relative to the X-ray detector for a different series of fringe patterns in order to acquire reference scan data during an imaging operation without the object in the examination region.

The grating arrangement can be moved for example to at least four, for example 4 to 50 or 4 to 100, different positions relative to the X-ray detector. Preferably the grating arrangement is moved in the scanning motion to a number of different positions relative to the X-ray detector such that a certain field of view, e.g. the entire radiation-sensitive area of the X-ray detector, is covered between 3 to 10 times. Moving the grating arrangement in the scanning motion can for example be performed for at least three, for example 3 to 12, 3 to 30, or 3 to 50, different series of fringe patterns.

The method can furthermore comprise the step:

moving the grating arrangement in the scanning motion to the same positions relative to the X-ray detector used for acquiring the reference scan data for one of the series of fringe patterns in order to acquire object scan data during an imaging operation with the object in the examination region.

Preferably, only one scanning motion resulting in only one of the series of fringe patterns is used for acquiring the object scan data. Alternatively, two or more scanning motions resulting in two or more different series of fringe patterns can be used for acquiring the object scan data.

The method can be used for performing X-ray phase-contrast imaging and/or X-ray dark-field imaging. Gratings of the grating arrangement can be arranged and configured in order to allow performing X-ray phase-contrast imaging and/or X-ray dark-field imaging.

The method can be used to operate an X-ray imaging device comprising two gratings, three gratings, or more gratings in the grating arrangement. The method can comprise keeping the gratings in a fixed spatial relationship relative to each other during each scanning motion. The method can furthermore be used to operate an X-ray imaging device in which a source grating is arranged between the X-ray source and the examination region. The source grating can be one of the gratings of the grating arrangement. The different series of fringe patterns can for example be generated by changing a relative lateral position of the gratings to each other between subsequent scanning motions. The relative lateral position of the gratings to each other can for example be changed by an actuator, e.g. a piezoelectric actuator, or the like between subsequent motions.

The method can comprise a step of fitting a first function to the reference scan data in order to obtain parameters. The first function can for example be $J_{xy\alpha}(z)=I_{xy\alpha}(1+V_{xy\alpha}\cos(\phi_{xy\alpha}+2\pi z/p))$ with $J_{xy\alpha}(z)$ the reference scan data acquired at a pixel xy of the X-ray detector, for position $\alpha$ of the grating arrangement relative to the X-ray detector, in dependence of relative lateral position z of the gratings to each other, mean flux $I_{xy\alpha}$, fringe visibility $V_{xy\alpha}$, fringe phase $\phi_{xy\alpha}$, and grating period p.

The method can furthermore comprise a step of fitting the object scan data using the parameters obtained from the reference scan data in order to obtain an image of the object.

The method can comprise a step of fitting a second function to the object scan data in order to obtain the image of the object. The second function can for example be $K_{xy\alpha}=I_{xy\alpha}T_{xy}(1+V_{xy\alpha}D_{xy}\cos(\psi_{xy}+\phi_{xy\alpha}+2\pi z_0/p))$ with $K_{xy\alpha}$ the object scan data acquired at the pixel xy of the X-ray detector for the position $\alpha$ of the grating arrangement relative to the X-ray detector for relative lateral position $z_0$ of the gratings to each other, image of object transmission $T_{xy}$, dark-field $D_{xy}$, and differential phase $\psi_{xy}$.

In a further aspect of the present invention, a computer program for operating the X-ray imaging device according to claim 1 or any embodiment of the X-ray imaging device is presented. The computer program comprises program code means for causing a processor to carry out the method as defined in claim 13 or any embodiment of the method, when the computer program is run on the processor.

The computer program can also be used for operating the X-ray imaging device in order to perform X-ray phase-contrast imaging and/or X-ray dark-field imaging. In this case, the computer program comprises program code means for causing a processor to carry out the method as defined in claim 14 or any embodiment of the method, when the computer program is run on the processor.

Furthermore, a computer program for operating the X-ray imaging device according to claim 9 is presented. The computer program comprises program code means for causing the processing unit to carry out the method as defined in claim 13, 14, or any embodiment of the method, when the computer program is run on the processing unit.

In a further aspect, a computer-readable medium having stored the computer program of claim 15 is presented. Alternatively or additionally, the computer-readable medium can have the computer program according to any embodiment of the computer program stored.

It shall be understood that the X-ray imaging device of claim 1, the method of claim 13, the computer program of claim 15, and the computer-readable medium have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
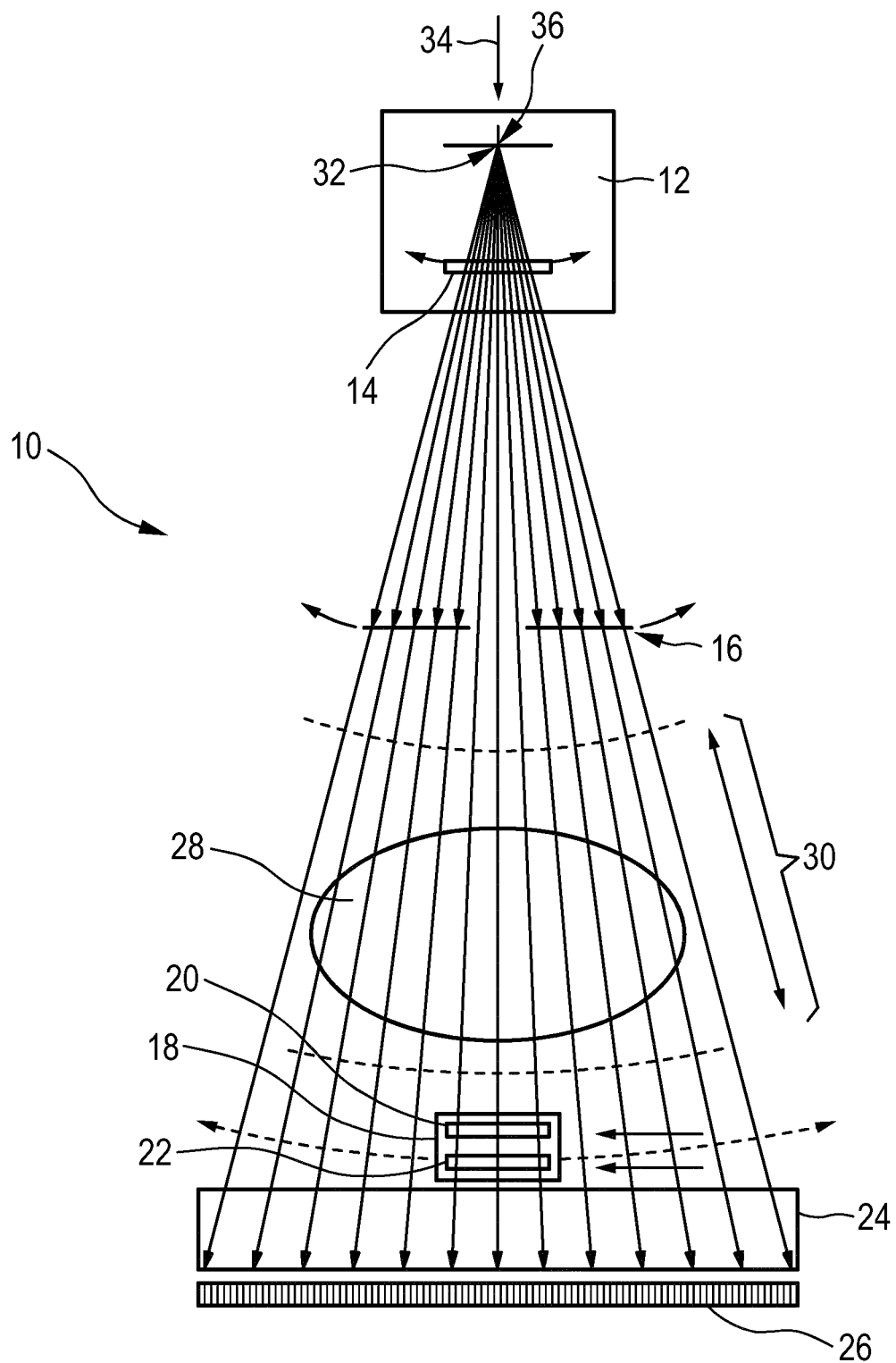
FIG. 1 shows schematically and exemplarily a first embodiment of an X-ray imaging device.

FIG. 1 shows schematically and exemplarily a first embodiment of an X-ray imaging device 10. The X-ray imaging device 10 can for example be used for X-ray phase-contrast imaging and/or dark-field imaging.

The X-ray imaging device 10 comprises an X-ray source 12, source grating 14, a collimator 16, a grating arrangement 18 with phase grating 20 and analyzer grating 22, an anti-scatter grid 24, and an X-ray detector 26. The X-ray imaging device 10 allows to image an object 28 arranged in an examination region 30, which is located between the X-ray source 12 and the X-ray detector 26.

As the footprint of the grating arrangement 18 on the X-ray detector 26 is smaller than a radiation-sensitive area of the X-ray detector 26 during an imaging operation with the X-ray imaging device 10, object scan data is only acquired for pixels xy in the radiation-sensitive area of the X-ray detector 26 provided with X-ray radiation showing the fringe pattern. The X-ray imaging device 10 therefore comprises a scan arm (not shown) for rotating the source grating 14, the collimator 16 and the grating arrangement 18 in a scanning motion relative to the X-ray detector 26 around rotation axis 32. This allows to acquire object scan data for the entire radiation-sensitive area and thus for all pixels xy of the X-ray detector 26.

In other embodiments, the source grating 14 can be part of the grating arrangement 18 (not shown). In yet other embodiments, the X-ray imaging device 10 can comprise a grating arrangement with only one grating if the X-ray detector has a spatial period of pixels sufficiently small for detecting the fringe pattern generated by the phase grating for the purpose of X-ray phase-contrast imaging and/or dark-field imaging. For that purpose, the X-ray detector can for example be a high resolution X-ray detector with a spatial resolution of 5 µm or an even better spatial resolution.

The X-ray source 12 emits a beam of X-ray radiation along optical axis 34 starting from focal spot 36. The optical axis 34 is an imaginary line that defines the path along which the central X-ray beam during imaging operation propagates from the focal spot 36 of the X-ray source 12 towards the X-ray detector 26, and along which the beam of X-ray radiation exhibits some form of symmetry.

In this embodiment, the rotation axis 32 runs through the focal spot 36 of the X-ray source 12.

The X-ray source 12 is of sealed-tube type in this embodiment. Alternatively, the X-ray source 12 may also be of rotating-anode type. The emission spectrum of the X-ray source 12 may be in the range of 25 kVp to 160 kVp and is in this embodiment a polychromatic tungsten spectrum.

The source grating 14 is arranged at an egress window of a housing of the sealed X-ray tube of the X-ray source 12 such that the source grating 14 generates a plurality of beams of individually coherent X-ray radiation which can be incoherent to each other. In other embodiments the source grating 14 can be arranged in or at the X-ray source 12 such that it allows to generate at least partly coherent X-ray radiation. In yet other embodiments, the X-ray source, e.g. a synchrotron (not shown), generates a native coherent beam of X-ray radiation that is sufficiently coherent such that no source grating is required for ensuring spatial coherence of the X-ray radiation in order to generate a fringe pattern. The source grating 14 has in this embodiment a period of 60 µm. The source grating 14 can have periods between 1 m and 500 µm. The source grating has a dimension of 4 mm times 40 mm in this embodiment. The dimension of the source grating 14 can be between 2 mm times 2 mm and 500 mm times 500 mm, for example between 4 mm times 40 mm and 10 mm times 100 mm. A footprint of the source grating 14 in the plane of the radiation-sensitive surface of the X-ray detector 26 can be as large as the dimensions of the X-ray detector 26. The footprint of the source grating 14 can for example be between 20 mm times 20 mm and 1000 mm times 1000 mm, as the footprint of the source grating 14 depends on the distance between the X-ray source 12 and source grating 14 as well as on the distance between the source grating 14 and the X-ray detector 26. The source grating 14 has a rectangular form in this embodiment. In other embodiments the source grating 14 can also have a quadratic form or any other form, such as a circular form.

In this embodiment, the X-ray detector 26 is a planar two-dimensional X-ray detector with 2900 times 2900 pixels xy for detecting X-ray radiation. Alternatively a planar or curved X-ray detector with any other number of pixels can be used, e.g., between 500 times 500 pixels and 10000 times 10000 pixels. The X-ray detector 26 in this embodiment has a dimension of 426 mm times 426 mm. Alternatively an X-ray detector with any other dimension can be used that has a radiation-sensitive area larger than the footprint of the gratings, e.g., between 20 mm times 20 mm and 1000 mm times 1000 mm, such as between 300 mm times 300 mm and 500 mm times 500 mm. The pixel size of the X-ray detector 26 in this embodiment is 148 µm times 148 µm. The pixel size can also for example be between 5 µm times 5 µm and 500 µm times 500 µm, such as between 100 µm times 100 µm and 500 µm times 500 µm for other X-ray detectors. In this embodiment, the X-ray detector 26 has a quadratic form. In other embodiments, the X-ray detector can have any other form, e.g., circular form or rectangular form. The X-ray detector can also be made from a number of line detectors, i.e. one dimensional X-ray detectors arranged parallel to each other to form a two-dimensional array of pixels xy.

The collimator 16 is optional. The collimator 16 has one slot and is made of a radiodense material in the form of lead. In other embodiments the collimator can be made of other radiodense materials. As the collimator 16 is arranged between the X-ray source 12 and the examination region 30, the beam of X-ray radiation can be made conform to the dimensions of the gratings 20 and 22 or footprint of the grating arrangement 18.

The phase grating 20 is a phase shift grating and may in other embodiments be replaced by an absorption grating. The phase grating 20 modulates onto the X-ray radiation a fringe pattern. The analyzer grating 22 is an absorption grating. Therefore the analyzer grating 22 acts as a transmission mask for the X-ray detector 26 and transforms local fringe position into signal intensity variation detectable by the X-ray detector 26. The detected intensity signal contains quantitative information about the phase shift induced by the object 28 arranged in the examination region 30. Using the analyzer grating 22 thus allows the X-ray detector 26 to have a lower resolution to resolve the fringe pattern. The gratings can be manufactured by photo lithographically processing suitable substrates such as silicon wafer. A pattern or periodic rulings can be formed in the substrates. The periodic rulings can be filled with absorbing materials, such as gold or the like. The phase grating 20 in this embodiment has a period of 9 µm. The phase grating can also have periods between 1 µm and 50 µm. In this embodiment the analyzer grating 22 has a period of 10 µm. The analyzer grating can also have periods between 1 µm and 100 µm. The analyzer grating 22 can have a period smaller than the pixel size of the X-ray detector 26. In this embodiment the phase grating 20 and analyzer grating 22 have the same dimension. In other embodiments the dimensions of the phase grating and analyzer grating can be different from each other. The dimension of the gratings 20 and 22 can be between 10 mm times 10 mm and 500 mm times 500 mm. The dimension of the gratings 20 and 22 is chosen such that the footprint of the gratings 20 and 22 on the X-ray detector 26 covers at least the whole length or height of the X-ray detector 26 in order to allow providing fringe patterns to the whole radiation-sensitive area of the X-ray detector 26 during scanning motions. In this embodiment the gratings 20 and 22 have a dimension of 10 mm times 426 mm. The gratings 20 and 22 in this embodiment have a rectangular form. The gratings 20 and 22 can also have any other form for example a quadratic or a circular form.

The anti-scatter grid 24 is optional. In this embodiment the anti-scatter grid 24 comprises a series of alternating strips of radiodense material in the form of lead and radiolucent material in the form of plastic. In other embodiments lead can be replaced by another radiodense material and plastic can be replaced by another radiolucent material. The primary X-ray beam radiation passes through the radiolucent material strips as it travels essentially parallel to the radiolucent material strips. Scattered radiation which deviates from the parallel beam path is attenuated by the radiodense material strips. Therefore the anti-scatter grid 24 allows to limit the amount of scatter radiation.

The object 28 arranged in the examination region 30 in this embodiment is a patient. Alternatively the object 28 may also be a piece of luggage, a microchip, a vegetable, or any other object that a user wants to examine.

In order to acquire an image of the object 28 an imaging operation has to be performed. Therefore first a reference scan without the object 28 in the examination region 30 is performed.

In the reference scan, imaging operation is performed by activating the X-ray source 12 which emits a beam of X-ray radiation which is made at least partly coherent by the source grating 14. This partly coherent X-ray radiation passes through the collimator 16 which narrows the beam in order to conform to the footprint of the grating arrangement 18 on the X-ray detector 26. The beam of X-ray radiation passes the examination region 30 without object 28 and interacts with the phase grating 20 which modulates a fringe pattern onto the X-ray radiation. The fringe pattern hits the analyzer grating 22 which acts as a transmission mask for the X-ray detector 26 and transforms local fringe position into signal intensity variation that is subsequently detected by the X-ray detector 26 at its pixels xy.

In order to acquire reference scan data for all pixels of the X-ray detector 26 the grating arrangement 18 is moved in a scanning motion to a number of different positions relative to the X-ray detector 26. In this embodiment the grating arrangement 18 is moved to 50 different positions by rotating it with the scan arm (not shown). In alternative embodiments the grating arrangement 18 can also be moved to any number of different positions between 4 and 100 different positions, for example to 10, 20, or 100 different positions. Hence the scan arm (not shown) rotates the source grating 14, collimator 16, phase grating 20, and analyzer grating 22 of the grating arrangement 18 around the rotation axis 32 relative to the radiation-sensitive surface of the X-ray detector 26 to acquire a series of fringe patterns for the different positions of the grating arrangement 18 relative to the X-ray detector 26.

In order to allow to separate phase information of the object 28 to be imaged from other contributions to the signal detected by the X-ray detector 26, such as absorption in the object 28, tolerances in the gratings or inhomogeneous illumination by the X-ray source 12, in the reference scan a number of different series of fringe patterns are acquired at the same positions of the grating arrangement 18 relative to the X-ray detector 26. In this embodiment the number of different series of fringe patterns acquired is 8. In alternative embodiments the number of different series of fringe patterns can for example be any number between 3 and 50, between 3 and 30, or between 3 and 12. The different series of fringe patterns can be generated by changing the relative lateral position of the gratings 14, 20 and 22 to each other, or changing the position of the focal spot 36 of the X-ray source 12 relative to the gratings 14, 20, 22 and the X-ray detector 26, e.g., by moving the focal spot 36 of the X-ray source 12 in a direction perpendicular to the optical axis 34. The focal spot 36 of the X-ray source 12 can for example be moved by an electromagnetic or magnetic field (not shown). In this embodiment the relative lateral position of the analyzer grating 22 to the phase grating 20 and source grating 14 is changed (not shown). Therefore a piezoelectric actuator (not shown) moves the analyzer grating 22 relative to the phase grating 20 along the transverse direction perpendicular to the grating lines in order to acquire images over one period of the analyzer grating 22. In other embodiments gratings 20 and 22 may also be rotated together around an axis oriented along the direction of the grating lines by an angle (not shown). Instead of the piezoelectric actuator any other actuator or the like may be provided.

The analyzer grating 22 is only moved relative to the gratings 14 and 20 between subsequent scanning motions. During one scanning motion, in which the source grating 14 and the gratings 20 and 22 of the grating arrangement 18 are moved to the different positions, the gratings 14, 20, and 22 remain in a fixed spatial relationship relative to each other.

The reference scan data is used to obtain reference parameters. In this embodiment a fitting function is used for fitting the reference scan data in order to obtain the reference parameters. The reference parameters can subsequently be used for fitting the object scan data acquired during an imaging operation with the object 28 in the examination region 30 in order to obtain an image of the object 28.

The object scan data is acquired by arranging the object 28 in the examination region 30 and activating the X-ray source 12. The beam of at least partly coherent X-ray radiation is narrowed by the collimator 16, passes through the examination region 30 and interacts with the object 28. The object 28 due to its structure and material modulates attenuation information, refraction information and small angle scattering information onto the X-ray radiation which can be extracted by operation of the phase grating 20 and the analyzer grating 22, in which the phase grating 20 modulates a fringe pattern onto the X-ray radiation which can be subsequently detected by the X-ray detector 26 after passing the analyzer grating 22 as fringes of a Moiré pattern. The Moiré pattern corresponds to a disturbed version of the reference pattern acquired during the reference scan. The difference from the reference pattern can be used to compute the images of attenuation, phase-contrast and dark-field. Signal processing is performed in a processing unit (not shown).

In order to acquire object scan data for all pixels of the X-ray detector 26 the grating arrangement 18 is moved in the scanning motion to the same positions relative to the X-ray detector 26 used for acquiring the reference scan data for only one of the series of fringe patterns. Thus the X-ray imaging device 10 acquires the object scan data during an imaging operation with the object 28 in the examination region 30.

The X-ray detector 26 is stationary during the whole imaging operation while the scan arm moves the collimator 16 and the gratings 14, 20 and 22 during the scanning motion.

In this embodiment the distance between the source grating 14, phase grating 20, and analyzer grating 22 are tuned to fit the requirements of Talbot distance which is a function of the spatial period of the grating rulings, also called pitch of the respective grating. Therefore the gratings function as a Talbot-Lau type interferometer. The requirements for configuring the gratings in order to function as a Talbot-Lau type interferometer are for example disclosed in EP 1 731 099 A1. In other embodiments in which the phase grating is replaced by an absorption grating, such that the X-ray imaging device comprises two absorption gratings other requirements apply, such as the requirements as disclosed for example in Huang et al. "Alternative method for differential phase-contrast imaging with weakly coherent hard x rays", Phys. Rev. A 79, 013815 (2009). In one embodiment the grating periods match in projection geometry.

In this embodiment the scan arm performs a pendulum like motion across the radiation-sensitive surface of the X-ray detector 26. Therefore also the gratings 14, 20 and 22 perform this pendulum like motion. This motion is similar to the one presented for the second embodiment of the X-ray imaging device 10' in FIG. 2A. Alternatively the motion may be along a straight path similar to the scanning motion performed for the third embodiment of the X-ray imaging device 10" in FIG. 3B.

In the first embodiment of the X-ray imaging device 10 presented in FIG. 1, the X-ray source 12 is not rotated together with the scan arm. In the fourth embodiment of the X-ray imaging device as shown in FIG. 4 to 9 the X-ray source 12 is rotated together with scan arm 38. This allows to increase flux.

In the first embodiment of the X-ray imaging device 10 presented in FIG. 1, the object 28 is in a lying position. The object 28 is placed on an object support (not shown). The object support can be moved in a direction perpendicular to the direction of the scanning motion, such that scanning the object in a meandering track like fashion is possible.

In other embodiments the source grating and the phase grating can also be arranged on the side of the X-ray source, such that the examination region is sandwiched between the phase grating and the analyzer grating (not shown), this arrangement is called inverse geometry. The phase grating can also be replaced by an absorption grating, the source grating can be removed or the phase grating can be replaced by an absorption grating and the source grating can be removed. The inverse geometry allows flexibility in adjusting dark-field sensitivity, as the sensitivity can be reduced by reducing the distance between the object and the analyzer grating.

Figure 2A:
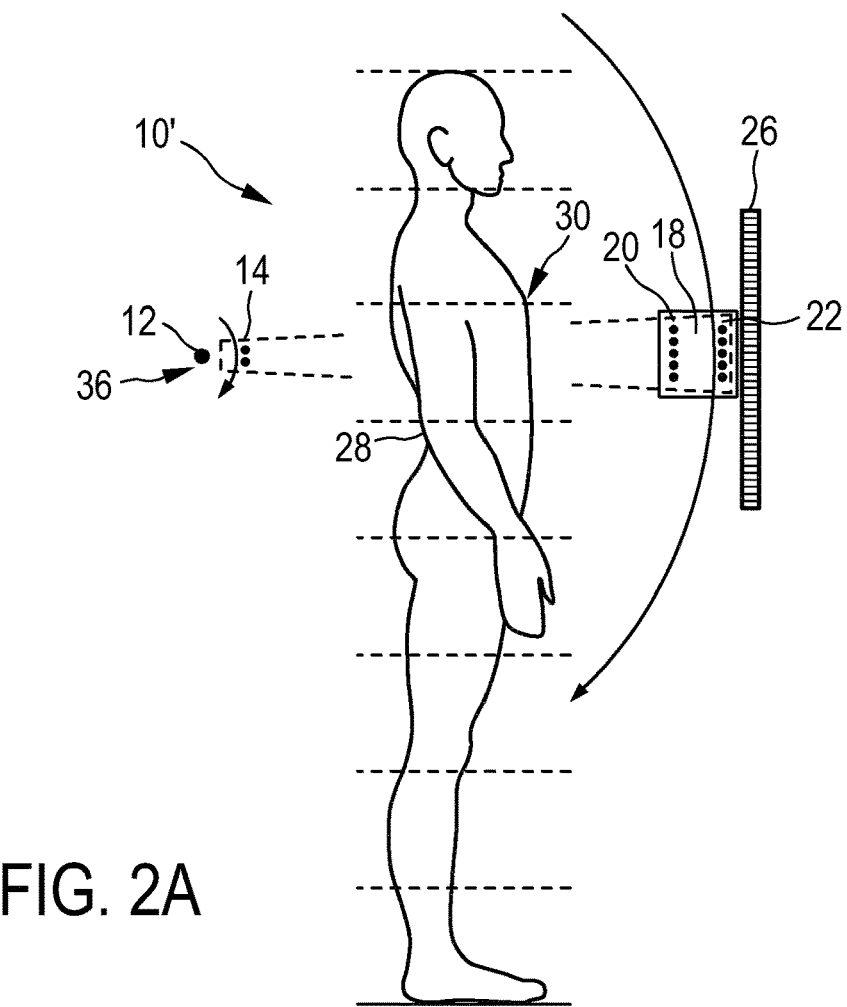
FIG. 2A shows schematically and exemplarily a second embodiment of the X-ray imaging device in a side view.
Figure 2B:
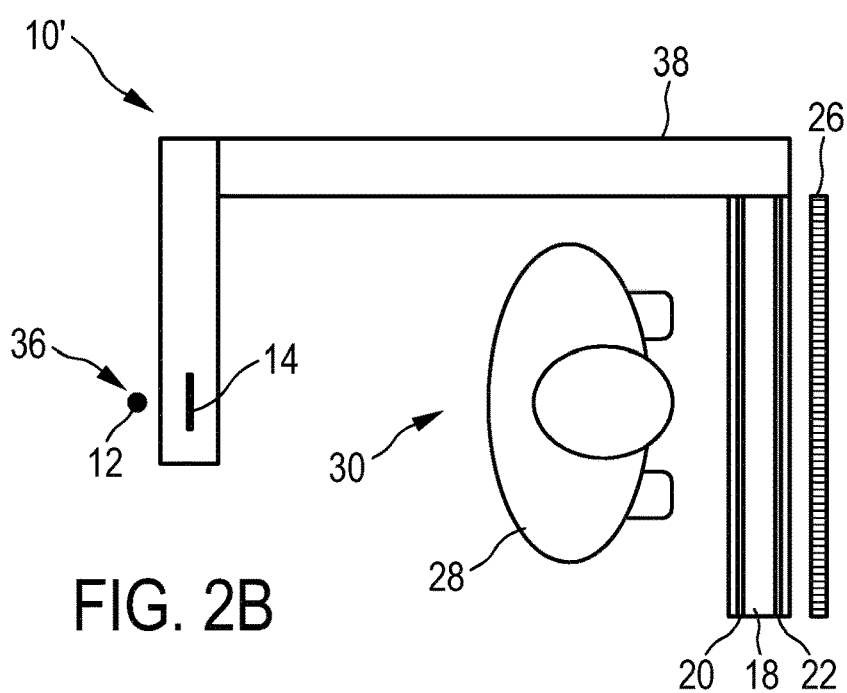
FIG. 2B shows schematically and exemplarily the second embodiment of the X-ray imaging device in a top-view.
Figure 2C:
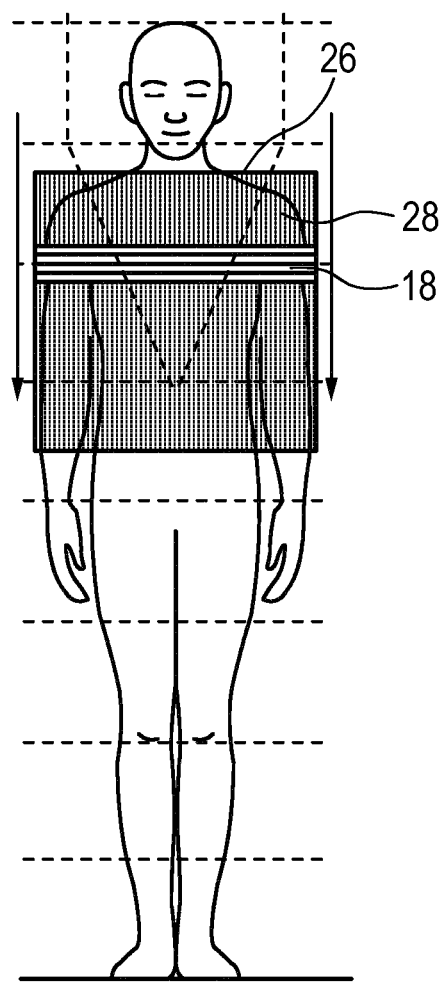
FIG. 2C shows schematically and exemplarily the second embodiment of the X-ray imaging device in a front view.

FIGS. 2A, 2B and 2C show schematically and exemplarily a second embodiment of the X-ray imaging device 10'.

The X-ray imaging device 10' comprises an X-ray source 12, source grating 14, a grating arrangement 18 with phase grating 20 and analyzer grating 22, as well as an X-ray detector 26. The source grating 14 can also be part of the grating arrangement 18 or the source grating 14 can also be removed. In other embodiments the phase grating and analyzer grating can be replaced by two absorption gratings.

An object 28, in this case an upright standing patient is arranged in the examination region 30. In this embodiment a chest of the patient is arranged in the examination region 30 for X-ray phase-contrast imaging.

X-ray radiation is provided from focal spot 36 of the X-ray source 12 to the X-ray detector 26.

The source grating 14 and the grating arrangement 18 with phase grating 20 and analyzer grating 22 are in this embodiment arranged at a scan arm 38. The scan arm 38 allows to rotate the source grating 14 and grating arrangement 18 relative to the X-ray detector 38. Hence during a scanning motion the three gratings 14, 20, and 22 remain in a fixed spatial relationship to each other. In this embodiment phase grating 20 and analyzer grating 22 have the same horizontal dimension as a radiation-sensitive surface of the X-ray detector 26 (see FIG. 2B) while the vertical dimension of the gratings 20 and 22 of grating arrangement 18 is smaller than the vertical dimension of the radiation-sensitive area of the X-ray detector 26 (see schematic FIG. 2A and schematic FIG. 2C). Hence also the grating arrangement 18 has the same horizontal dimension as the radiation-sensitive surface of the X-ray detector 26 while the vertical dimension of the grating arrangement 18 is smaller than the vertical dimension of the radiation-sensitive area of the X-ray detector 26.

FIG. 2A shows the X-ray imaging device 10' in a side view, FIG. 2B shows the X-ray imaging device 10' in a top-view, and FIG. 2C shows the X-ray imaging device 10' in a front view.

The second embodiment of the X-ray imaging device 10' is particularly useful for chest imaging of a patient.

FIG. 3 shows schematically and exemplarily a third embodiment of the X-ray imaging device 10".

Figure 3A:
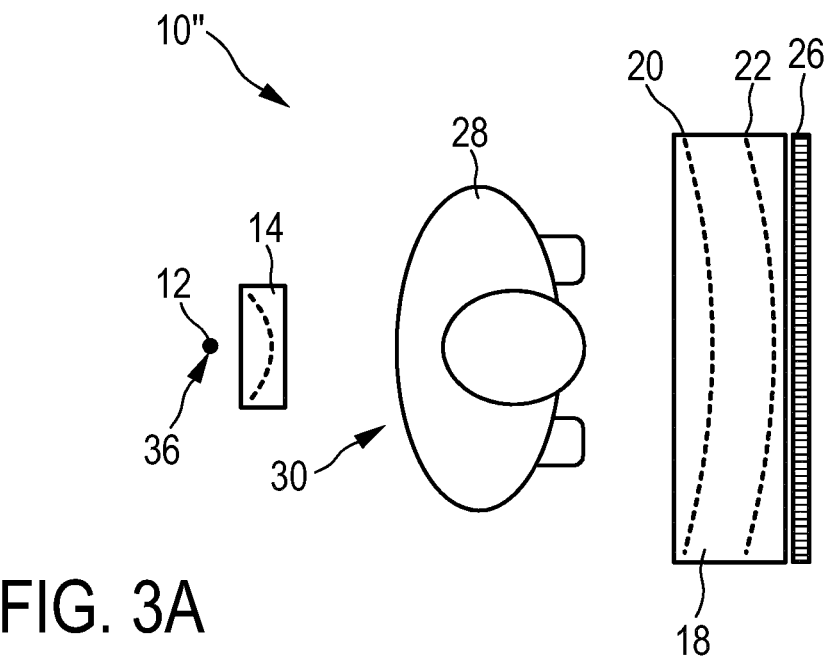
FIG. 3A shows schematically and exemplarily a third embodiment of the X-ray imaging device in a top-view.

The X-ray imaging device 10" in contrast to the second embodiment of the X-ray device 10' has curved source grating 14, curved phase grating 20 and curved analyzer grating 22 as can be seen in FIG. 3A. The curved form of the gratings allows rulings of the gratings to be aligned to focal spot 36 of X-ray source 12 such that the rulings of the gratings 14, 20, and 22 are aligned along vertical scan direction. In other embodiments, the curved source grating, phase grating and analyzer grating can be replaced by two curved absorption gratings or a curved source grating and two curved absorption gratings.

Figure 3B:
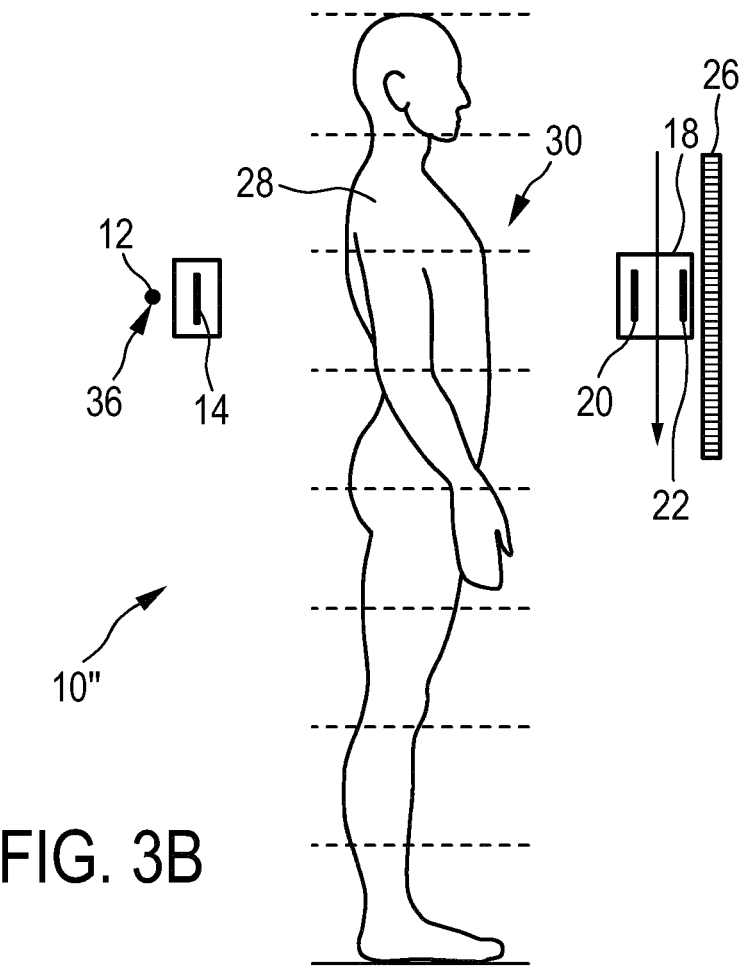
FIG. 3B shows schematically and exemplarily the third embodiment of the X-ray imaging device in a side view.

For the imaging operation grating arrangement 18 with the gratings 20 and 22 moves in a scanning motion to different positions along a straight path relative to X-ray detector 26. As the rulings of the gratings 14, 20, and 22 run parallel to the scanning direction, it is possible to keep the source grating 14 fixed during the scanning motion as can be seen in FIG. 3B. Additionally the X-ray source 12 and the X-ray detector 26 are stationary.

Further details relating to scanning motions along a linear path can be found in WO 2017/001294 A1 in particular in FIG. 11 of WO 2017/001294 A1 and its corresponding description.

FIG. 4 to 9 show schematically and exemplarily a fourth embodiment of the X-ray imaging device 10''' with scan arm 38 in different positions α and gratings 14, 20, and 22 in different relative lateral positions z to each other.

The X-ray imaging device 10''' comprises X-ray source 12, source grating 14, grating arrangement 18 with phase grating 20 and analyzer grating 22, an X-ray detector 26, and a processing unit 40.

In other embodiments the source grating 14 is part of the grating arrangement 18 or removed (not shown). In other embodiments the phase grating 20 and analyzer grating 22 can be replaced by two absorption gratings.

A beam of X-ray radiation is provided from the focal spot 36 of the X-ray source 12 with a central beam that propagates along optical axis 34 passing the source grating 14, an examination region 30 in which an object 28 can be arranged, the grating arrangement 18 with phase grating 20 and analyzer grating 22 and hitting the X-ray detector 26. The X-ray detector 26 provides signals generated from detected X-ray radiation to the processing unit 40. In this embodiment the X-ray detector 26 is connected with processing unit 40 by wire. Alternatively the processing unit 40 may be connected wirelessly to the X-ray detector 26.

The X-ray source 12, source grating 14, and grating arrangement 18 are arranged at the scan arm 38. The scan arm 38 is rotatable. In this embodiment the scan arm 38 can be rotated around a rotation axis 32 that extends through the focal spot 36 of the X-ray source. In other embodiments the X-ray source may be arranged outside the scan arm (not shown).

Figure 4:
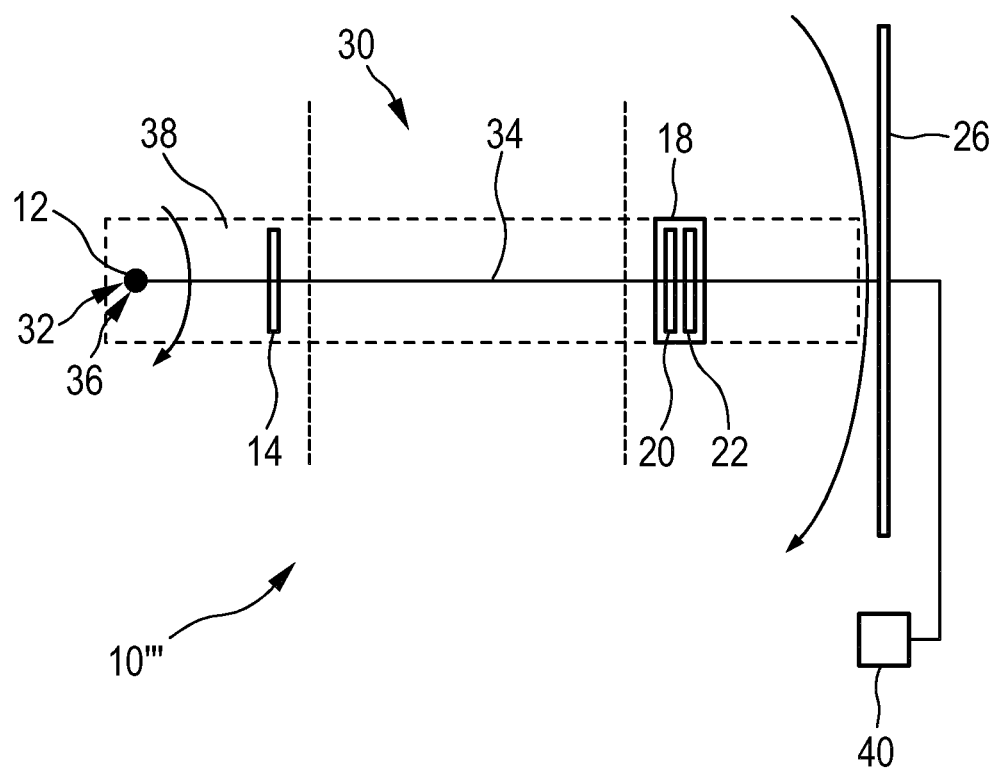
FIG. 4 shows schematically and exemplarily a fourth embodiment of the X-ray imaging device with scan arm in a first position and gratings in a first relative lateral position to each other.
Figure 5:
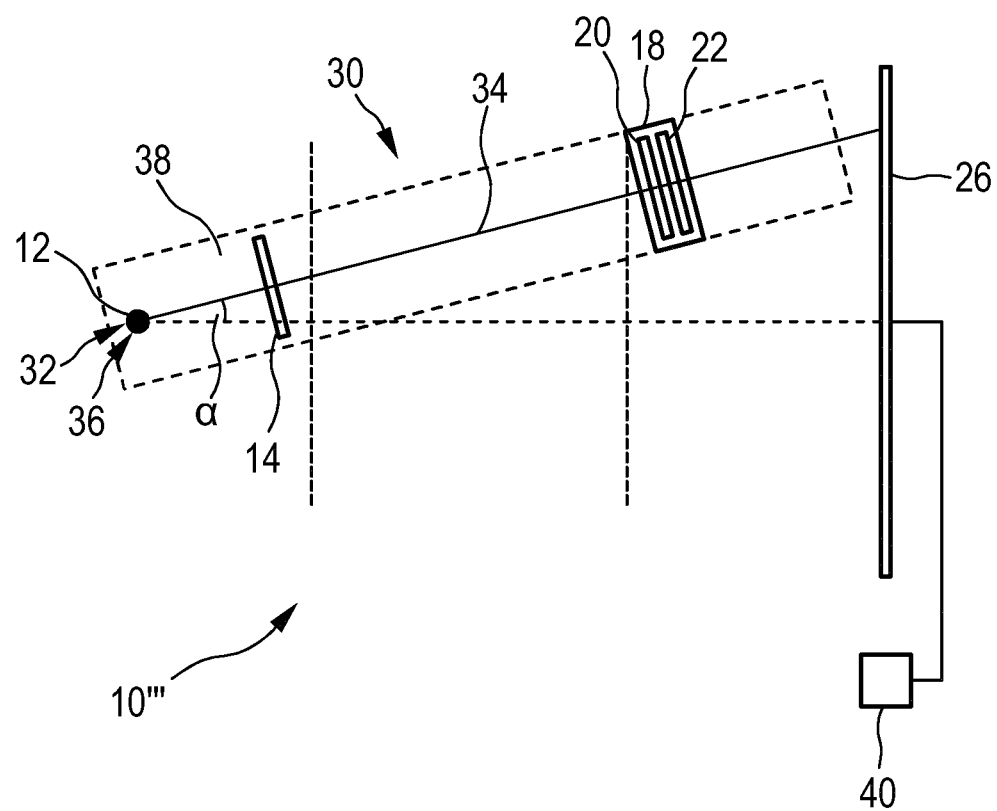
FIG. 5 shows schematically and exemplarily the fourth embodiment of the X-ray imaging device with scan arm in a second position.
Figure 6:
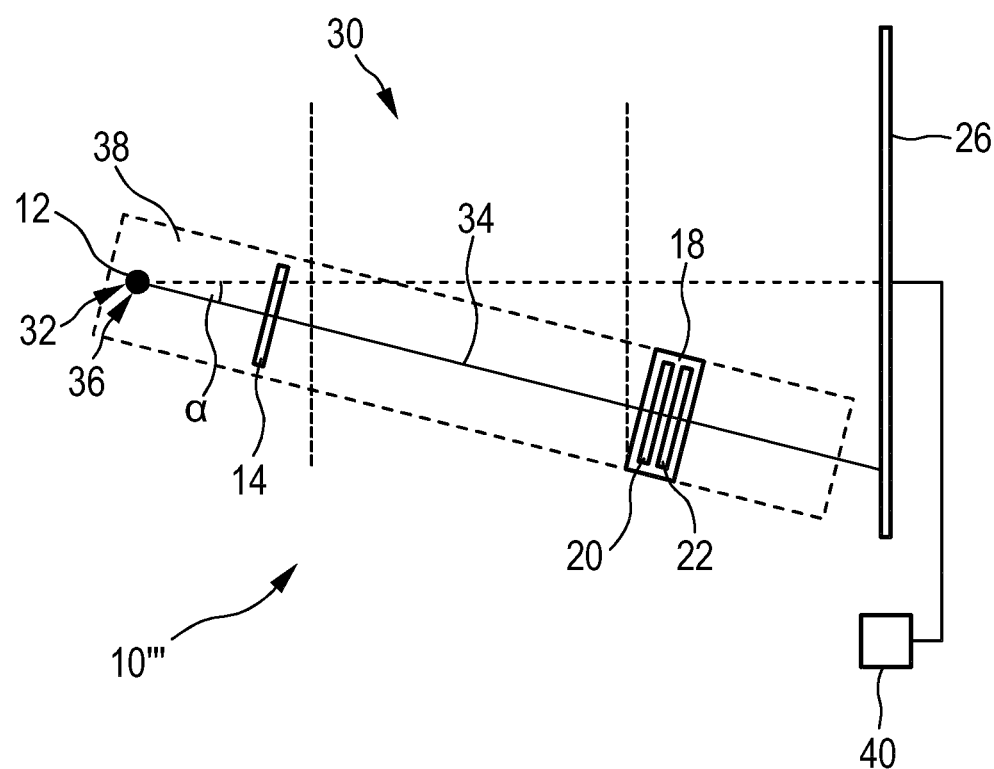
FIG. 6 shows schematically and exemplarily the fourth embodiment of the X-ray imaging device with scan arm in a third position.

In FIG. 4 the scan arm 38 and the grating arrangement 18 with gratings 20 and 22 arranged at the scan arm 38 are moved to a first position relative to the X-ray detector 26. In FIG. 5 the scan arm 38 is rotated such that the grating arrangement 18 with gratings 20 and 22 is moved to a second position $\alpha$ relative to the X-ray detector 26. In FIG. 6 another rotation of the scan arm 38 allows to move the grating arrangement 18 with gratings 20 and 22 to a third position $\alpha$ relative to the X-ray detector 26. Rotating the scan arm 38 allows to move the grating arrangement 18 with gratings 20 and 22 to different positions relative to the X-ray detector 26 and therefore to perform imaging of the examination region 30. Furthermore it allows to provide each of the pixels xy of the X-ray detector 26 with a fringe pattern.

Figure 9:
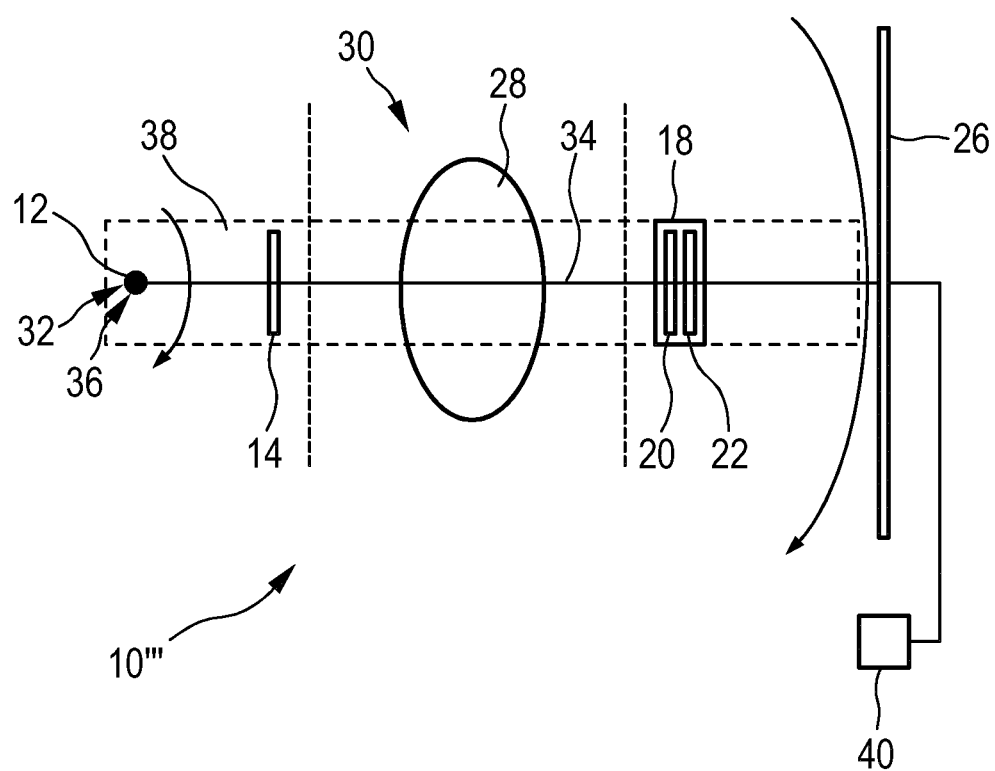
FIG. 9 shows schematically and exemplarily the fourth embodiment of the X-ray imaging device with scan arm in the first position, gratings in the first relative lateral position to each other, and an object in the examination region.

The X-ray imaging device 10''' performs essentially the same imaging operation as described for the first embodiment of the X-ray imaging device 10. However, X-ray imaging device 10''' does not have a collimator and does not have an anti-scatter grid. Therefore the X-ray imaging device 10''' performs a reference scan to acquire reference scan data without an object 28 in the examination region, as shown in FIG. 4 to 8. Subsequently an object scan can be performed for acquiring object scan data with an object 28 in the examination region, as shown in FIG. 9.

The reference scan data is acquired by rotating the grating arrangement 18 in a scanning motion to 50 different positions $\alpha$, i.e., in this embodiment rotation angles $\alpha$, relative to the X-ray detector 26 whilst the X-ray detector 26 remains stationary relative to the examination region 30 such that in the scanning motion a series of fringe patterns is detected by the X-ray detector 26 and by repeating the rotation of the grating arrangement 18 in the scanning motion to the same positions $\alpha$ relative to the X-ray detector 26 for seven different series of fringe patterns. In other embodiments the reference scan data can also be acquired by rotating the grating arrangement 18 in a scanning motion to another number of different positions $\alpha$ relative to the X-ray detector 26, e.g. to a number of different positions between 4 and 100, or between 20 and 100, for example to 10, 20, or 100 different positions. The rotation of the grating arrangement 18 in the scanning motion to the same positions $\alpha$ relative to the X-ray detector 26 can also be repeated for another number of different series of fringe patterns, e.g., for 2 or more different series of fringe patterns, or any number between 2 and 50, between 2 and 30, or between 2 and 12, such as 2, 4, 7, or 11 different series of fringe patterns. Increasing the number of fringe patterns increases the accuracy of the derived reference parameters and thus improves the final image quality at the cost of longer acquisition times for the imaging operation for acquiring the reference scan data.

Figure 7:
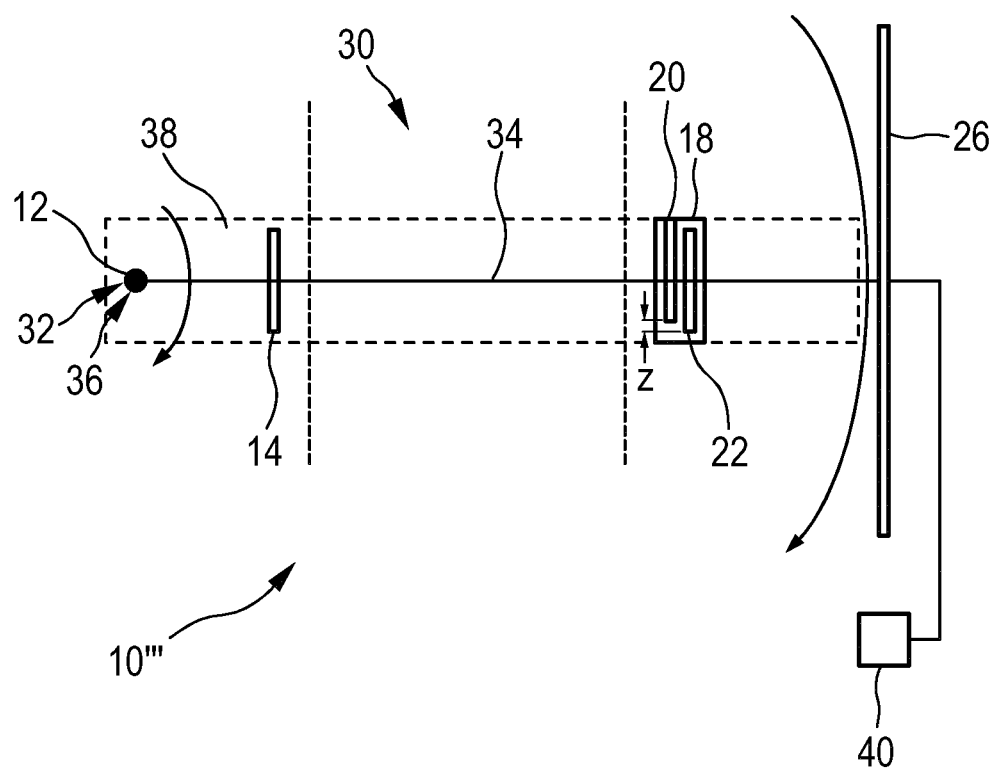
FIG. 7 shows schematically and exemplarily the fourth embodiment of the X-ray imaging device with scan arm in the first position and gratings in a second relative lateral position to each other.
Figure 8:
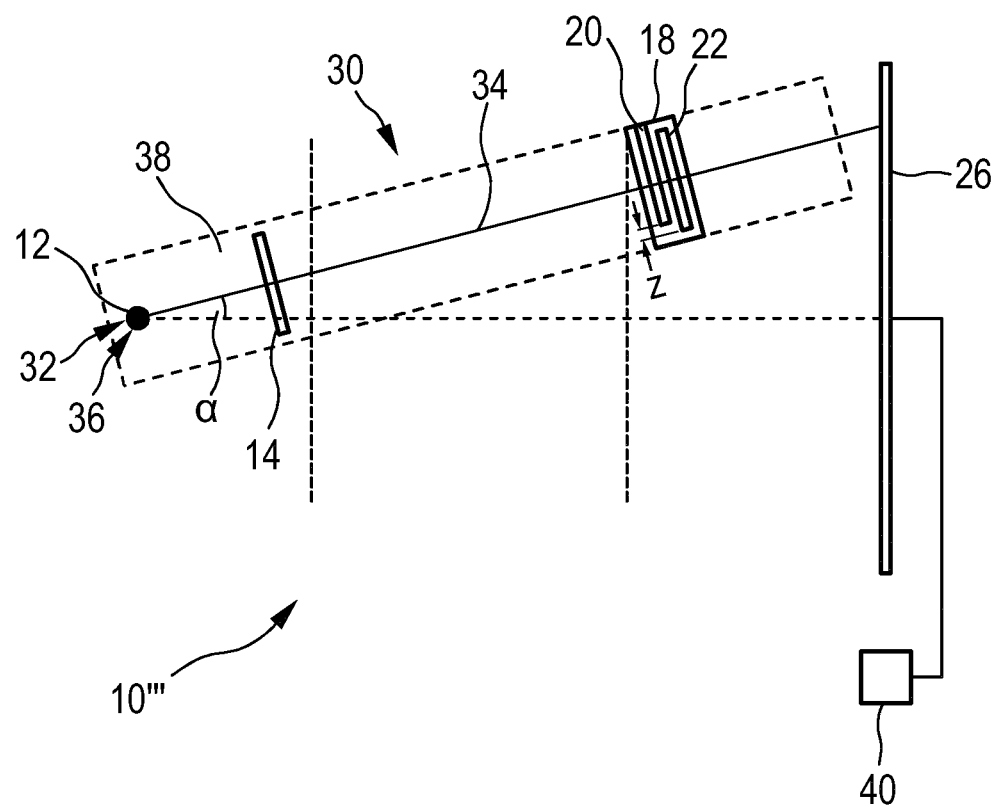
FIG. 8 shows schematically and exemplarily the fourth embodiment of the X-ray imaging device with scan arm in the second position and gratings in the second relative lateral position to each other.

In this embodiment of the X-ray imaging device 10''' the series of fringe patterns is generated by changing the relative lateral position z of the gratings 14, 20, and 22 to each other. In particular FIG. 7 shows the X-ray imaging device 10''' with the scan arm 38 in the first position and the gratings 14, 20, and 22 in a second relative lateral position z to each other, i.e. the phase grating 20 is shifted with regard to the other two gratings 14 and 22. Therefore the fringe pattern is changed and hence also the signal acquired by the X-ray detector 26. The phase grating 20 is moved by a piezoelectric actuator (not shown) relative to the source grating 14 and the analyzer grating 22 along the transverse direction perpendicular to the grating lines in order to acquire images over one period of the phase grating 20. The phase grating 20 is only moved between subsequent scanning motions. Therefore a scanning motion is performed by moving the grating arrangement 18 via the scan arm 38 to the different positions relative to the X-ray detector 26. Then the phase grating 20 is moved relative to the other gratings 14 and 22. Subsequently the next scanning motion is performed by moving the grating arrangement 18 to the same positions relative to the X-ray detector 26 as in the previous scanning motion. This allows to acquire reference scan data which can be resorted to obtain a full phase-stepping curve for every pixel xy of the X-ray detector 26. The reference scan data is provided to the processing unit 40 for resorting and processing.

The processing unit 40 processes the reference scan data by fitting a first function to the reference scan data in order to obtain reference parameters. The processing unit 40 uses least-squares fit. In other embodiments the processing unit 40 can also use any other fitting method such as weighted least-squares. In this embodiment the processing unit 40 uses the first fitting function $J_{xy\alpha}(z)=I_{xy\alpha}(1+V_{xy\alpha}\cos(\phi_{xy\alpha}+2\pi z/p))$ to fit the reference scan data, with $J_{xy\alpha}(z)$ the reference scan data acquired at a pixel xy of the X-ray detector 26 for rotation angle $\alpha$ of the grating arrangement 18 relative to the X-ray detector 26 in dependence of the relative lateral position z of the gratings 14, 20 and 22 to each other, mean flux $I_{xy\alpha}$, fringe visibility $V_{xy\alpha}$, fringe phase $\phi_{xy\alpha}$, and grating period p of the phase grating 20, in order to obtain the reference parameters.

Object scan data is acquired during an imaging operation with the object 28 in the examination region 30 by rotating the grating arrangement 18 with gratings 20 and 22 in the scanning motion to the same positions $\alpha$ relative to the X-ray detector 26 used for acquiring the reference scan data for only one of the series of fringe patterns. The object scan data is provided to the processing unit 40 for processing.

The processing unit 40 fits a second function to the object scan data using the reference parameters obtained from the reference scan data. Therefore the processing unit 40 uses the second function $K_{xy\alpha}=I_{xy\alpha}T_{xy}(1+V_{xy\alpha}D_{xy}\cos(\psi_{xy}+\phi_{xy\alpha}+2\pi z_0/p))$ to fit the object scan data, with $K_{xy\alpha}$ the object scan data acquired at the pixel xy of the X-ray detector 26 for the rotation angle $\alpha$ of the grating arrangement 18 relative to the X-ray detector 26 for the relative lateral position $z_0$ of the gratings 14, 20, and 22 to each other, image of object transmission $T_{xy}$, dark-field $D_{xy}$, and differential phase $\psi_{xy}$. Thus image of object transmission, dark-field and differential phase can be acquired by fitting the second function. The X-ray imaging device 10''' allows to reduce the number of scan motions for acquiring reference scan data and object scan data and therefore requires less time for imaging.

Figure 10:
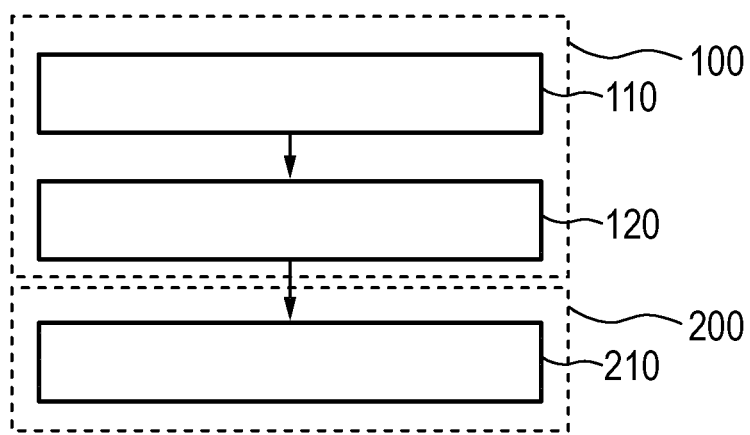
FIG. 10 shows an embodiment of a method for operating an X-ray imaging device.

FIG. 10 shows an embodiment of the method for operating an X-ray imaging device. The X-ray imaging device is provided as follows.

An X-ray source for emitting a beam of X-ray radiation is provided. The X-ray source in this embodiment is an X-ray tube and has a source grating for generating a plurality of beams of individually coherent X-ray radiation which can be incoherent to each other. Alternatively a native coherent X-ray source can be provided, such as a synchrotron. In other embodiments the source grating can also be separated from the X-ray source. In yet other embodiments no source grating is provided.

An X-ray detector is arranged opposite the X-ray source across an examination region for accommodating an object to be imaged.

A grating arrangement is arranged between the X-ray source and the X-ray detector. Furthermore the grating arrangement is configured to modulate onto the X-ray radiation a fringe pattern detectable by the X-ray detector. Furthermore the grating arrangement is configured such that the grating arrangement has a footprint on the X-ray detector that is smaller than a radiation-sensitive area of the X-ray detector. In order to configure the grating arrangement two absorption gratings are provided and the absorption gratings are arranged such that the footprint on the X-ray detector is smaller than a radiation-sensitive area of the X-ray detector and such that a fringe pattern detectable by the X-ray detector is modulated onto the X-ray radiation. In other embodiments the grating arrangement comprises a phase grating to modulate onto the X-ray radiation a fringe pattern and an analyzer grating that supports the X-ray detector for detecting the fringe pattern. Alternatively only one grating or three or more gratings may be provided. One or more of the gratings can also be absorption gratings. The source grating can also be provided as a grating of the grating arrangement. It is to be understood that the footprint of the grating arrangement depends on the size of a grating or gratings of the grating arrangement and the distance between the grating arrangement and the X-ray detector. Therefore configuring the grating arrangement such that the grating arrangement has a footprint on the X-ray detector that is smaller than a radiation-sensitive area of the X-ray detector, includes both providing a grating arrangement of certain size and arranging the grating arrangement in a certain distance from the X-ray detector, such that the grating arrangement has a footprint on the X-ray detector that is smaller than a radiation-sensitive area of the X-ray detector.

For acquiring the reference scan data the method performs a first module 100 with steps 110 and 120.

In step 110 the grating arrangement is moved in a scanning motion to a number of different positions relative to the X-ray detector. The gratings are kept in a fixed spatial relationship to each other during the scanning motion. In this embodiment the grating arrangement is rotated around a rotation axis for moving it to the different positions which in this embodiment are 50 different positions relative to the X-ray detector. In another embodiment the different positions can for example be any number of different positions between 4 and 100 different positions, for example 10, 20, or 100 different positions relative to the X-ray detector. The X-ray detector is kept stationary relative to the examination region during the scanning motion such that in the scanning motion a series of fringe patterns is detected by the X-ray detector. Hence while the position of the fringe pattern moves over the radiation-sensitive area of the X-ray detector different pixels xy of the X-ray detector can detect different fringe patterns. In this embodiment a series of fringe patterns is detected, as the rotation of the grating arrangement generates an angle between radiation-sensitive surface of the X-ray detector and the gratings of the grating arrangement generating the fringe pattern, such that the fringe pattern is slightly different for the different positions in the scanning motion due to magnification.

In step 120 moving the grating arrangement in the scanning motion to the same positions relative to the X-ray detector is repeated for a number of different series of fringe patterns in order to acquire reference scan data during an imaging operation without the object in the examination region. The different series of fringe patterns are in this embodiment generated by changing a relative lateral position of the gratings to each other between subsequent scanning motions. The relative lateral position of the gratings to each other between subsequent motions can for example be changed by a piezoelectric actuator or the like. Hence in this embodiment the phase grating is moved relative to the analyzer grating. In this embodiment the number of different series of fringe patterns is 8. The number of different series of fringe patterns can also for example be any number above 3 or any number between 3 and 50, between 3 and 30, or between 3 and 12, such as 3, 5, 8, or 12. Reference scan data can thus be acquired for every pixel xy of the X-ray detector. This allows to obtain a full phase-stepping curve for every pixel xy of the X-ray detector.

After acquiring the reference scan data an optional second module 200 for performing X-ray phase-contrast imaging and/or X-ray dark-field imaging can be performed.

The object is arranged in the examination region before performing step 210.

In step 210 the grating arrangement is moved in the scanning motion to the same positions relative to the X-ray detector used for acquiring the reference scan data for only one of the series of fringe patterns in order to acquire object scan data during an imaging operation with the object in the examination region. Alternatively two or more scan motions resulting in two or more different series of fringe patterns can be used for acquiring the object scan data.

The steps 110 and 120 are essential for acquiring reference scan data. Step 210 is optional and can be used for performing X-ray phase-contrast imaging and/or X-ray dark-field imaging in order to obtain an image of the object.

In an alternative embodiment module 200 furthermore comprises a step of fitting a first function to the reference scan data in order to obtain parameters. The first function can for example be $J_{xy\alpha}(z)=I_{xy\alpha}(1+V_{xy\alpha}\cos(\phi_{xy\alpha}+2\pi z/p))$ with $J_{xy\alpha}(z)$ the reference scan data acquired at a pixel xy of the X-ray detector for position $\alpha$ of the grating arrangement relative to the X-ray detector in dependence of relative lateral position z of the gratings to each other, mean flux $I_{xy\alpha}$, fringe visibility $V_{xy\alpha}$, fringe phase $\phi_{xy\alpha}$, and grating period p. The alternative embodiment furthermore comprises a step of fitting the object scan data using the parameters obtained from the reference scan data in order to obtain an image of the object. Therefore the alternative embodiment comprises a step of fitting a second function to the object scan data in order to obtain the image of the object. The second function can for example be $K_{xy\alpha}=I_{xy\alpha}T_{xy}(1+V_{xy\alpha}D_{xy}\cos(\psi_{xy}+\phi_{xy\alpha}+2\pi z_0/p))$ with $K_{xy\alpha}$ the object scan data acquired at the pixel xy of the X-ray detector for the position $\alpha$ of the grating arrangement relative to the X-ray detector for relative lateral position $z_0$ of the gratings to each other, image of object transmission $T_{xy}$, dark-field $D_{xy}$, and differential phase $\psi_{xy}$.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein an X-ray source and a phase grating or absorption grating have a footprint that has the same size as a radiation-sensitive area of an X-ray detector while the footprint of an analyzer grating is smaller than the radiation-sensitive area of the X-ray detector. In this case only the analyzer grating has to be moved in a scanning motion while the other components can be stationary.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit, processor, or device may fulfill the functions of several items recited in the claims. The mere fact that certain measures are recited in mutually different dependent claims does not indicate that a combination of these measures cannot be used to advantage.

Operations like moving the grating arrangement in a scanning motion to a number of different positions relative to the X-ray detector, keeping the X-ray detector stationary relative to the examination region, detecting in the scanning motion a series of fringe patterns by the X-ray detector, moving the grating arrangement in the scanning motion to the same positions relative to the X-ray detector for a number of different series of fringe patterns without the object in the examination region, moving the grating arrangement in the scanning motion to the same positions relative to the X-ray detector used for acquiring the reference scan data for one of the series of fringe patterns with the object in the examination region, et cetera performed by one or several units or devices can be performed by any other number of units or devices. These operations and/or the method can be implemented as program code means of a computer program and/or as dedicated hardware.

A computer program may be stored/distributed on a suitable medium, such as an optical storage medium, or a solid-state medium, supplied together with or as part of other hardware, but may also be distributed in other forms, such as via the Internet, Ethernet, or other wired or wireless telecommunication systems.

Any reference signs in the claims should not be construed as limiting the scope.

The present invention relates to acquiring reference scan data for X-ray phase-contrast imaging and/or X-ray dark-field imaging. Therefore an X-ray detector is arranged opposite an X-ray source across an examination region with a grating arrangement arranged between the X-ray source and the X-ray detector. During an imaging operation without an object in the examination region the grating arrangement is moved in a scanning motion to a number of different positions relative to the X-ray detector whilst the X-ray detector remains stationary relative to the examination region such that in the scanning motion a series of fringe patterns is detected by the X-ray detector. The scanning motion is repeated for a different series of fringe patterns. This allows acquiring reference scan data required for calibration of an X-ray imaging device with less scanning motions.

The invention claimed is:

1. An X-ray imaging device, comprising:
an X-ray source for emitting a beam of X-ray radiation;
an X-ray detector arranged opposite the X-ray source across an examination region for accommodating an object to be imaged;
a grating arrangement arranged between the X-ray source and the X-ray detector and configured to modulate onto the X-ray radiation a fringe pattern detectable by the X-ray detector;
wherein a footprint of the grating arrangement on the X-ray detector is smaller than a radiation-sensitive area of the X-ray detector, and
wherein the X-ray imaging device is configured to acquire reference scan data during an imaging operation without the object in the examination region:
by moving the grating arrangement in a scanning motion to a number of different positions, in a motion path direction, relative to the X-ray detector whilst the X-ray detector remains stationary relative to the examination region, such that in the scanning motion a series of fringe patterns is detected by the X-ray detector, and
by moving the grating arrangement in the scanning motion to the same positions, in the motion path direction, relative to the X-ray detector for a different series of fringe patterns, such that phase information is separated from other information.

2. The X-ray imaging device according to claim 1, wherein the X-ray imaging device is configured to acquire object scan data during the imaging operation with the object in the examination region by moving the grating arrangement in the scanning motion to the same positions relative to the X-ray detector used for acquiring the reference scan data for one of the series of fringe patterns.

3. The X-ray imaging device according to claim 2, wherein the X-ray imaging device is configured to fit the object scan data based on parameters obtained from the reference scan data in order to obtain an image of the object.

4. The X-ray imaging device according to claim 3, wherein the grating arrangement is arranged at least partly in the beam of X-ray radiation during the imaging operation for performing phase-contrast imaging and/or dark-field imaging.

5. The X-ray imaging device according to claim 4, wherein the grating arrangement comprises two gratings, and wherein the gratings remain in a fixed spatial relationship relative to each other during each of the scanning motions.

6. The X-ray imaging device according to claim 5, further comprising a source grating arranged between the X-ray source and the examination region, such that the source grating generates a plurality of beams of individually coherent X-ray radiation which can be incoherent to each other.

7. The X-ray imaging device according to claim 5, wherein the X-ray imaging device is configured to generate different series of fringe patterns by changing a relative lateral position of the gratings to each other between subsequent scanning motions.

8. The X-ray imaging device according to claim 7, further comprising a processor configured to process the reference scan data and the object scan data by fitting a first function to the reference scan data in order to obtain the parameters and by fitting a second function to the object scan data using the parameters obtained from the reference scan data.

9. The X-ray imaging device according to claim 8, wherein the processor is configured for fitting the first function to the reference scan data based on relative lateral position of the gratings to each other, mean flux, fringe visibility, fringe phase, and/or grating period.

10. The X-ray imaging device according to claim 9, wherein the processor is configured for fitting the second function to the object scan data for relative lateral position of the gratings to each other, image of object transmission, dark-field, and/or differential phase.

11. The X-ray imaging device according to claim 10, wherein the two gratings of the grating arrangement are a phase grating and an absorption grating, and wherein a distance between the gratings is tuned to fit the requirements of Talbot distance such that the grating arrangement forms a Talbot-Lau type interferometer.

12. The X-ray imaging device according to claim 1, wherein the X-ray imaging device is configured to acquire the reference scan data during the imaging operation without the object in the examination region by moving the grating arrangement in a scanning motion to at least four different positions relative to the X-ray detector whilst the X-ray detector remains stationary relative to the examination region, such that in the scanning motion a series of fringe patterns is detected by the X-ray detector, and by moving the grating arrangement in the scanning motion to the same positions relative to the X-ray detector for at least two different series of fringe patterns.

13. The X-ray imaging device of claim 1, wherein the motion path direction is a lateral direction perpendicular to an axis direction in which the X-ray source and the X-ray detector are spaced apart from each other.

14. The X-ray imaging device of claim 1, wherein the different series of fringe patterns are detected by the X ray detector at the same positions, in the motion path direction, of the grating arrangement relative to the X-ray detector.

15. A method for operating an X-ray imaging device, comprising:
   providing an X-ray source for emitting a beam of X-ray radiation;
   providing an X-ray detector arranged opposite the X-ray source across an examination region for accommodating an object to be imaged;
   providing a grating arrangement arranged between the X-ray source and the X-ray detector and configured to modulate onto the X-ray radiation a fringe pattern detectable by the X-ray detector; and
   acquiring reference scan data during an imaging operation without the object in the examination region;
   by moving the grating arrangement in a scanning motion to a number of different positions, in a motion path direction, relative to the X-ray detector while keeping the X-ray detector stationary relative to the examination region, such that in the scanning motion a series of fringe patterns is detected by the X-ray detector; and
   by moving the grating arrangement in the scanning motion to the same positions, in the motion path direction, relative to the X-ray detector for a different series of fringe patterns, such that phase information is separated from other information.

16. The method according to claim 15, further comprising:
   moving the grating arrangement in the scanning motion to the same positions relative to the X-ray detector used for acquiring the reference scan data for one of the series of fringe patterns in order to acquire object scan data during an imaging operation with the object in the examination region.

17. A non-transitory computer-readable medium having one or more executable instructions stored thereon which, when executed by at least one processor, cause the at least one processor to perform a method for operating an X-ray imaging device, the method comprising:
   providing an X-ray source for emitting a beam of X-ray radiation;
   providing an X-ray detector arranged opposite the X-ray source across an examination region for accommodating an object to be imaged;
   providing a grating arrangement arranged between the X-ray source and the X-ray detector and configured to modulate onto the X-ray radiation a fringe pattern detectable by the X-ray detector; and
   acquiring reference scan data during an imaging operation without the object in the examination region;
   by moving the grating arrangement in a scanning motion to a number of different positions, in a motion path direction, relative to the X-ray detector while keeping the X-ray detector stationary relative to the examination region, such that in the scanning motion a series of fringe patterns is detected by the X-ray detector; and
   by moving the grating arrangement in the scanning motion to the same positions, in the motion path direction, relative to the X-ray detector for a different series of fringe patterns, such that phase information is separated from other information.

* * * * *